United States Patent [19]

Ryono et al.

[11] Patent Number: 4,629,724

[45] Date of Patent: Dec. 16, 1986

[54] AMINO ACID ESTER AND AMIDE RENIN INHIBITORS

[75] Inventors: Denis E. Ryono, Princeton; Edward W. Petrillo, Jr., Pennington, both of N.J.

[73] Assignee: E. R. Squibb & Sons, Inc., Princeton, N.J.

[21] Appl. No.: 677,714

[22] Filed: Dec. 3, 1984

[51] Int. Cl.$^4$ .................. A61K 37/43; C07K 7/02; C07K 5/08
[52] U.S. Cl. ............................. 514/18; 530/332; 530/330
[58] Field of Search ............ 260/112.5 R; 514/18; 530/332, 330

[56] References Cited

U.S. PATENT DOCUMENTS

| | | | |
|---|---|---|---|
| 4,470,973 | 9/1984 | Natarajan et al. | 424/177 |
| 4,514,391 | 4/1985 | Gordon et al. | 260/112.5 R |
| 4,539,312 | 9/1985 | Delaney et al. | 260/112.5 R |

FOREIGN PATENT DOCUMENTS 104041  3/1984  European Pat. Off. .

Primary Examiner—Delbert R. Phillips
Attorney, Agent, or Firm—Lawrence S. Levinson; Stephen B. Davis

[57] ABSTRACT

Compounds of the formula

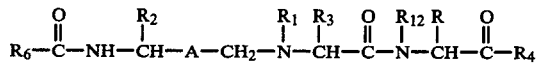

wherein A is

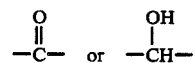

intervene in the conversion of angiotensinogen to angiotensin II by inhibiting renin and thus are useful as anti-hypertensive agents.

21 Claims, No Drawings

AMINO ACID ESTER AND AMIDE RENIN INHIBITORS

BACKGROUND OF THE INVENTION

Szelke et al. in European Patent Application No. 104,041 disclose renin inhibitory polypeptides including the partial sequence $$X-A-B-Z-W$$

wherein
A is $$-NH-\overset{R^1}{\underset{|}{CH}}-G-\overset{R^3}{\underset{|}{N}}-\overset{R^2}{\underset{|}{CH}}-\overset{O}{\underset{||}{C}}-$$

and G is $$-\overset{O}{\underset{||}{C}}-CH_2- \text{ or } -\overset{OH}{\underset{|}{CH}}-CH_2-,$$

X is hydrogen, protecting group or an amino acyl residue,
B is a lipophilic amino acyl residue, and
Z plus W are an amino alcohol residue or
Z is aminoacyl and
W is hydroxy, ester, amide, etc.

Natarajan et al. in U.S. Pat. No. 4,470,973 disclose aminoketone carboxylic acids of the formula $$R_2-\overset{O}{\underset{||}{C}}-NH-\overset{}{\underset{|}{CH}}-\overset{O}{\underset{||}{C}}-CH_2-\overset{R}{\underset{|}{N}}-\overset{R_1}{\underset{|}{CH}}-\overset{O}{\underset{||}{C}}-OH$$
$$\phantom{R_2-\overset{O}{\underset{||}{C}}-NH-}\underset{R_3}{|}$$

as intermediates in the preparation of aminoketone peptides which possess angiotensin converting enzyme or enkephalinase inhibition activity.

Gordon et al. in United States Application No. Ser. No. 515,729 filed July 21, 1983, now U.S. Pat. No. 4,514,391, disclose hydroxy substituted peptide compounds of the formula $$R_2-\overset{O}{\underset{||}{C}}-NH-\overset{}{\underset{|}{CH}}-\overset{OH}{\underset{|}{CH}}-CH_2-\overset{R}{\underset{|}{N}}-\overset{R_1}{\underset{|}{CH}}-\overset{O}{\underset{||}{C}}-X$$
$$\phantom{R_2-\overset{O}{\underset{||}{C}}-NH-}\underset{R_3}{|}$$

which possess angiotensin converting enzyme or enkephalinase inhibition activity.

SUMMARY OF THE INVENTION

This invention is directed to new amino acid ester and amide compounds of formula I including pharmaceutically acceptable salts thereof $$R_6-\overset{O}{\underset{||}{C}}-NH-\overset{R_2}{\underset{|}{CH}}-A-CH_2-\overset{R_1}{\underset{|}{N}}-\overset{R_3}{\underset{|}{CH}}-\overset{O}{\underset{||}{C}}-\overset{R_{12}}{\underset{|}{N}}-\overset{R}{\underset{|}{CH}}-\overset{O}{\underset{||}{C}}-R_4 \quad (I)$$

wherein:

A is $$-\overset{OH}{\underset{|}{CH}}- \text{ or } -\overset{O}{\underset{||}{C}}-.$$

$R_4$ is —O-lower alkyl, —O—$(CH_2)_m$-aryl, —OH, —O—$(CH_2)_m$-heterocyclo, or $$-\overset{H}{\underset{|}{N}}-R_5.$$

$R_5$ is hydrogen, lower alkyl, —$(CH_2)_m$—aryl, or —$(CH_2)_m$—hetero.
m is zero, one, two, three or four.
$R_6$ is lower alkyl, —$(CH_2)_m$—aryl, —$(CH_2)_m$—heterocyclo, or $$R_8-NH-\overset{}{\underset{R_7}{\underset{|}{CH}}}-.$$

$R_8$ is hydrogen, $$(H_3C)_3-C-O-\overset{O}{\underset{||}{C}}-, \quad \text{phenyl}-CH_2-O-\overset{O}{\underset{||}{C}}-,$$

$$\text{lower alkyl}-\overset{O}{\underset{||}{C}}-, \quad \text{cycloalkyl-}(CH_2)_m-\overset{O}{\underset{||}{C}}-,$$

$$\text{aryl-}(CH_2)_m-\overset{O}{\underset{||}{C}}-, \quad \text{heterocyclo-}(CH_2)_m-\overset{O}{\underset{||}{C}}-,$$

$$\text{aryl-O}-CH_2-\overset{O}{\underset{||}{C}}-, \text{ or } R_{10}-NH-\overset{R_9}{\underset{|}{CH}}-\overset{O}{\underset{||}{C}}-.$$

$R_{10}$ is hydrogen, $$(H_3C)_3-C-O-\overset{O}{\underset{||}{C}}-, \quad \text{phenyl}-CH_2-O-\overset{O}{\underset{||}{C}}-,$$

$$\text{lower alkyl}-\overset{O}{\underset{||}{C}}-, \quad \text{cycloalkyl-}(CH_2)_m-\overset{O}{\underset{||}{C}}-,$$

$$\text{aryl-}(CH_2)_m-\overset{O}{\underset{||}{C}}-, \quad \text{heterocyclo-}(CH_2)_m-\overset{O}{\underset{||}{C}}-, \text{ or }$$

$$\text{aryl-O}-CH_2-\overset{O}{\underset{||}{C}}-.$$

R, $R_2$, $R_3$, $R_7$ and $R_9$ are independently selected from the group consisting of hydrogen, lower alkyl, halo substituted lower alkyl, —$(CH_2)_n$—aryl, —$(CH_2)_n$—heterocyclo, —$(CH_2)_n$—OH, —$(CH_2)_n$—NH$_2$, —$(CH_2)_n$—SH, —$(CH_2)_n$—S—lower alkyl, —$(CH_2)_2$—S—$(CH_2)_2$—NH$_2$, $$-(CH_2)_n-NH-C\overset{\displaystyle NH}{\underset{\displaystyle NH_2}{\diagdown}}, \quad -(CH_2)_n-\overset{O}{\underset{||}{C}}-NH_2,$$

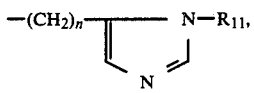

and —(CH$_2$)$_n$—cycloalkyl.

n is an integer from 1 to 4.

R$_{11}$ is

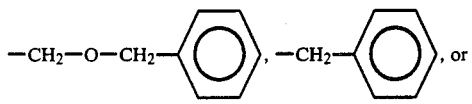

R$_1$ is hydrogen, lower alkyl, —(CH$_2$)$_n$—aryl, —(CH$_2$)$_n$—cycloalkyl,

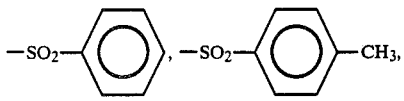

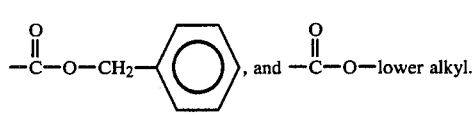

R$_{12}$ is hydrogen, lower alkyl, —(CH$_2$)$_n$—aryl, or —(CH$_2$)$_n$—cycloalkyl.

DETAILED DESCRIPTION OF THE INVENTION

This invention in its broadest aspects relates to the amino acid ester and amide compounds of formula I above, to compositions and the method of using such compounds as antihypertensive agents.

The term lower alkyl used in defining various symbols refers to straight or branched chain radicals having up to seven carbons, preferably from one to four carbons. Similarly, the terms lower alkoxy and lower alkylthio refer to such lower alkyl groups attached to an oxygen or sulfur.

The term cycloalkyl refers to saturated rings of 4 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halogen, hydroxy, amino, —NH—alkyl wherein alkyl is of 1 to 4 carbons, or —N(alkyl)$_2$ wherein alkyl is of 1 to 4 carbons, di or tri substituted phenyl, 1-naphthyl or 2-naphthyl wherein said substituents are methyl, methoxy, methylthio, halogen, or hydroxy.

The term heterocyclo refers to fully saturated or unsaturated rings of 5 or 6 atoms containing one or two O and S atoms and/or one to four N atoms provided that the total number of hetero atoms in the ring is 4 or less. The heterocyclo ring is attached by way of an available carbon atom. Preferred heterocyclo groups include 2- and 3-thienyl, 2- and 3-furyl, 2-, 3- and 4-pyridyl, and imidazolyl. The term heterocyclo also includes bicyclic rings wherein the five or six membered ring containing O, S and N atoms as defined above is fused to a benzene ring. The preferred bicyclic ring is indolyl.

Compounds of formula I wherein A is

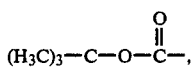

can be prepared as follows. A halomethyl ketone of the formula $$R_{40}-NH-\overset{R_2}{\underset{|}{CH}}-\overset{O}{\underset{\|}{C}}-CH_2-halo \quad (II)$$

wherein R$_{40}$ is a protecting group such as $$(H_3C)_3-C-O-\overset{O}{\underset{\|}{C}}-,$$

especially wherein halo is Cl, is reacted with an amine of the formula $$\overset{R_1}{\underset{|}{H}}-N-\overset{R_3}{\underset{|}{CH}}-\overset{O}{\underset{\|}{C}}-N-\overset{R_{12}}{\underset{|}{CH}}-\overset{R}{\underset{|}{C}}-\overset{O}{\underset{\|}{C}}-R_4. \quad (III)$$

This reaction is performed in the presence of sodium bicarbonate and dimethylformamide and gives the compound of the formula $$R_{40}-NH-\overset{R_2}{\underset{|}{CH}}-\overset{O}{\underset{\|}{C}}-CH_2-N-\overset{R_1}{\underset{|}{CH}}-\overset{R_3}{\underset{|}{C}}-\overset{O}{\underset{\|}{C}}-N-\overset{R_{12}}{\underset{|}{CH}}-\overset{R}{\underset{|}{C}}-\overset{O}{\underset{\|}{C}}-R_4. \quad (IV)$$

The intermediate of formula IV is then treated to remove the R$_{40}$ protecting group such as by treatment with hydrochloric acid in the presence of ethyl acetate and the resulting amine hydrochloride salt is reacted with the carboxylic acid of the formula $$R_6-COOH \quad (V)$$

in the presence of dicyclohexylcarbodiimide and hydroxybenzotriazole to give the desired final product.

The compounds of formula I wherein A is

can be prepared as follows. The intermediates of formula IV is treated with a conventional reducing agent such as sodium borohydride, sodium cyanoborohydride, diisobutyl aluminum hydride, lithium tri t-butoxy aluminum hydride, etc., to give $$R_{40}-NH-\underset{\underset{R_2}{|}}{CH}-\underset{\underset{OH}{|}}{CH}-CH_2-\underset{\underset{R_1}{|}}{N}-\underset{\underset{R_3}{|}}{CH}-\overset{\overset{O}{\|}}{C}-\underset{\underset{R_{12}}{|}}{N}-\underset{\underset{R}{|}}{CH}-\overset{\overset{O}{\|}}{C}-R_4.\quad\text{(VI)}$$

The intermediate of formula VI is then treated to remove the $R_{40}$ protecting group and the resulting amine is reacted with the carboxylic acid of formula V as described above to give the desired final products.

The compounds of formula I wherein A is $$-\underset{\underset{OH}{|}}{CH}-$$

can also be prepared by reacting an oxazolidine, trimethylsilylethyl ester of the formula (VII)

[Structure: Prot-N / HC—CH$_2$—N(R$_1$)—CH(R$_3$)—C(=O)—O—(CH$_2$)$_2$—Si(CH$_3$)$_3$, with CH-R$_2$ and H$_3$C—C(CH$_3$)—O forming oxazolidine ring]

so as to introduce the desired $$-\underset{\underset{R_{12}}{|}}{N}-\underset{\underset{R}{|}}{CH}-\overset{\overset{O}{\|}}{C}-R_4$$

substituent. For example, the ester of formula VII is treated with tetra n-butyl ammonium fluoride, followed by the amino acid, ester, or amide of the formula $$HN-\underset{\underset{R_{12}}{|}}{\phantom{N}}\underset{\underset{R}{|}}{CH}-\overset{\overset{O}{\|}}{C}-R_4 \quad\text{(VIII)}$$

in the presence of dicyclohexylcarbodiimide and hydroxybenzotriazole hydrate. The resulting oxazolidine is then treated with trifluoroacetic acid and aqueous hydrochloric acid to give the intermediate of the formula (IX)

$$HCl.H_2N-\underset{\underset{R_2}{|}}{CH}-\underset{\underset{OH}{|}}{CH}-CH_2-\underset{\underset{R_1}{|}}{N}-\underset{\underset{R_3}{|}}{CH}-\overset{\overset{O}{\|}}{C}-\underset{\underset{R_{12}}{|}}{N}-\underset{\underset{R}{|}}{CH}-\overset{\overset{O}{\|}}{C}-R_4.$$

The intermediate of formula IX is then treated with the carboxylic acid of formula V in the presence of dicyclohexylcarbodiimide and hydroxybenzotriazole as described above to give the desired final products.

In the above reactions, if $R_1$ is hydrogen then that N-atom would be protected for example by reacting the intermediate of formula IV with benzyloxycarbonyl chloride in the presence of pyridine and benzene. The benzyloxycarbonyl group could then be removed as the last step of the synthesis by hydrogenation in the presence of palladium on carbon catalyst.

Similarly, if any of R, $R_1$, $R_2$, $R_3$, $R_7$ and $R_9$ in the above reactions are —(CH$_2$)$_n$-aryl wherein aryl is phenyl, 1-naphthyl, 2-naphthyl substituted with one or more hydroxy or amino groups, —(CH$_2$)$_n$—heterocyclo wherein heterocyclo is an imidazolyl, —(CH$_2$)$_n$—NH$_2$, —(CH$_2$)$_n$—SH, —(CH$_2$)$_n$—OH, or $$-(CH_2)_n-NH-C\underset{\diagdown NH_2}{\overset{\diagup NH}{\phantom{C}}}$$

then the hydroxyl, amino, imidazolyl, mercaptan, or guanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or by other known means following completion of the reaction.

The starting materials of formula II can be prepared by reacting an N-protected amino acid of the formula $$R_{40}-NH-\underset{\underset{R_2}{|}}{CH}-COOH \quad\text{(X)}$$

with isobutylchloroformate, followed by diazomethane, and finally hydrochloric acid.

The oxazolidine, trimethylsilyl ethyl ester of formula VII can be prepared by reacting the halomethyl ketone of formula II with the amino acid, trimethylsilyl ester of formula $$HN-\underset{\underset{R_1}{|}}{\phantom{N}}\underset{\underset{R_3}{|}}{CH}-\overset{\overset{O}{\|}}{C}-O(CH_2)_2Si(CH_3)_3 \quad\text{(XI)}$$

in the presence of sodium iodide, sodium bicarbonate and dimethylformamide to give the compound of the formula $$R_{40}-NH-\underset{\underset{R_2}{|}}{CH}-\overset{\overset{O}{\|}}{C}-CH_2-\underset{\underset{R_1}{|}}{N}-\underset{\underset{R_3}{|}}{CH}-\overset{\overset{O}{\|}}{C}-O(CH_2)_2Si(CH_3)_3. \quad\text{(XII)}$$

The ketone of formula XII is reduced to the corresponding alcohol by treatment with sodium borohydride or other reducing agents as described above. This alcohol is then treated with 2-methoxypropene in the presence of a catalytic amount of pyridinium-p-toluenesulfonic acid to give the desired oxazolidine, trimethylsilyl ethyl ester.

The various peptide intermediates employed in above procedures are known in the literature or can be readily prepared by known methods. See for example, The Peptides, Volume 1, "Major Methods Of Peptide Bond Formation", Academic Press (1979).

Preferred compounds of this invention are those of formula I wherein:

A is $$-\underset{\underset{OH}{|}}{CH}-.$$

$R_1$ is hydrogen,

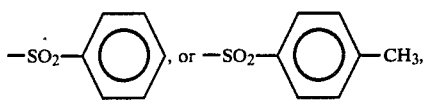

especially hydrogen.

R$_2$ is straight or branched chain lower alkyl of 1 to 4 carbons, benzyl, phenethyl, or

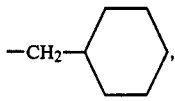

especially —CH$_2$—CH(CH$_3$)$_2$.

R$_3$ is hydrogen, straight or branched chain lower alkyl of 1 to 4 carbons, benzyl or phenethyl, especially —CH$_2$—CH(CH$_3$)$_2$ or —CH(CH$_3$)$_2$.

R$_{12}$ is hydrogen.

R is straight or branched chain lower alkyl of 1 to 4 carbons, benzyl or phenethyl, especially —CH(CH$_3$)$_2$ or benzyl.

R$_4$ is —O—lower alkyl wherein lower alkyl is straight or branched chain of 1 to 4 carbons, especially —O—CH$_3$.

R$_6$ is

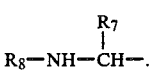

R$_7$ is

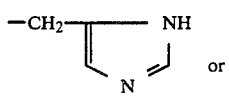

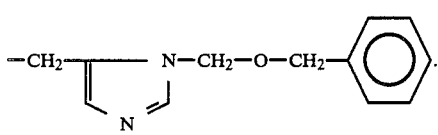

R$_8$ is hydrogen,

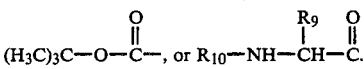

R$_9$ is —(CH$_2$)$_n$—aryl wherein aryl is phenyl or 1-naphthyl and n is one or two, especially

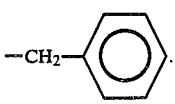

R$_{10}$ is hydrogen,

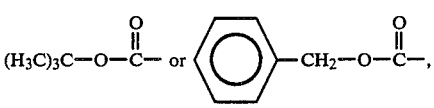

especially

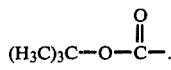

The compounds of formula I form salts with a variety of inorganic and organic acids. The non-toxic pharmaceutically acceptable salts are preferred, although other salts are also useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

The compounds of formula I contain asymmetric centers when any or all of R, R$_2$, R$_3$, R$_7$, and R$_9$ are other than hydrogen. An additional asymmetric center is present when A is

Thus, the compounds of formula I can exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The compounds of formula I, and the pharmaceutically acceptable salts thereof, are anti-hypertensive agents. They inhibit the conversion of angiotensinogen to angiotensin I and therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen⊔(renin)→angiotensin I→(ACE)→angiotensin II sequence by inhibiting renin and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 100 to 1000 mg., preferably about 250 to 500 mg. per kg. of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension.

A combination product comprising a compound of this invention and a diuretic can be administered in an effective amount which comprises a total daily dosage of about 1000 to 6000 mg., preferably about 3000 to 4000 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration or in sterile solutions or suspensions for parenteral administration. About 100 to 500 mg. of a compound of formula I is compounded with physiologically acceptable vehicle, carrier, excipient, binder, preservative, stabilizer, flavor, etc., in a unit dosage form as called for by acepted pharmaceutical practice. The amount of active substance in these compositions or preparations is such that a suitable dosage in the range indicated is obtained.

The following examples are illustrative of the invention. Temperatures are given in degrees centigrade.

EXAMPLE 1

(2R,3S)-N-[N-[3-(L-Histidylamino)-2-hydroxy-5-methylhexyl]-L-leucyl]-L-valine, methyl ester, hydrochloride (1:3.1)

(a) [(Phenylmethoxy)carbonyl]-L-leucine, 2-(trimethylsilyl)ethyl ester

A mixture of [(phenylmethoxy)carbonyl]-L-leucine (20.1 g., 75.7 mmole), dimethylaminopyridine (0.925 g., 7.57 mmole), and 2-(trimethylsilyl)ethanol (8.95 g., 75.7 mmole) in methylene chloride (200 ml.) is cooled in an ice-bath under nitrogen and treated with a solution of dicyclohexylcarbodiimide (15.6 g., 75.7 mmole) in 50 ml. of methylene chloride. The ice-bath is removed after 20 minutes and the reaction is allowed to come to room temperature overnight. The reaction mixture is filtered, concentrated in vacuo and partitioned between 800 ml. of ether and 200 ml. of water. The organic layer is separated and further rinsed with saturated sodium bicarbonate, water, 10% potassium bisulfate, water, and brine, dried (MgSO$_4$), and concentrated in vacuo to give 26.1 g. of crude product. Flash filtration over silica gel (180 g.in 20:1 hexane:ethyl acetate) yields 22.9 g. of crude product which is chromatographed using the Waters Prep 500 LC, two columns eluted with 15:1 hexane:ethyl acetate (250 ml./minute, 200 ml. fractions). Combining the pure product fractions yields 19.6 g. of [(phenylmethoxy)carbonyl]-L-leucine, 2-(trimethylsilyl)ethyl ester as an oil; $[\alpha]_D = -7.3°$ (c=1, chloroform). TLC (silica gel; 10:1 hexane:ethyl acetate) $R_f = 0.12$.

(b) L-Leucine, 2-(trimethylsilyl)ethyl ester 1 g. of 10% palladium on carbon catalyst is added to a solution of [(phenylmethoxy)carbonyl]-L-leucine, 2-(trimethylsilyl)ethyl ester (9.1 g., 24.9 mmole) in ethyl acetate (200 ml.) cooled in an ice-bath under nitrogen. The reaction mixture is subjected to a steady stream of hydrogen gas for 2.5 hours at room temperature, then filtered and concentrated in vacuo to remove volatiles and yield 5.8 g. of L-leucine, 2-(trimethylsilyl)-ethyl ester as a liquid product. TLC (silica gel, 3:1 hexane:ethyl acetate) $R_f = 0.08$.

(c) [(S)-1-Chloro-5-methyl-2-oxo-3-hexyl]carbamic acid, 1,1-dimethylethyl ester

N-Methyl-N'-nitro-N-nitrosoguanidine (24.2 g., 165 mmole) is added portionwise over a period of 30 minutes to a mixture of ether (275 ml.) and 40% aqueous potassium hydroxide (75 ml.) in a 1 l. Erlenmeyer flask cooled in a ice-water bath. Throughout the reaction the flask is magnetically stirred and loosely stoppered. At the end of the addition, the reaction is stirred cold for 45 minutes longer.

A solution of [(1,1-dimethylethoxy)carbonyl]-L-leucine hydrate (19.2 g., 77 mmole) in dry tetrahydrofuran (180 ml.) is cooled to −10° to −15° under an atmosphere of argon. The reaction mixture is treated with N-methylmorpholine (7.79 g., 77 mmole), added neat, followed by the careful addition of isobutylchloroformate (10.5 g., 77 mmole), added neat and dropwise while keeping the temperature between −10° and −15°. Upon completion of the addition, the solution is kept at −15° for 15 minutes before addition to the ethereal diazomethane.

As much as possible of the diazomethane solution in ether is decanted into a 1 l. Erlenmeyer flask and kept cold. The remainder is poured into a 500 ml. separatory funnel. The aqueous layer is drained and discarded while the ether is added to the decanted material. The total ethereal diazomethane is quickly dried over solid potassium hydroxide, then decanted into a 1 l. filtering flask fitted with an argon sidearm connection, magnetically stirred and cooled in a −10° bath. Total volume by now is about 400 ml. A filtering funnel is put in place with vacuum momentarily connected at sidearm, the mixed anhydride preparation is quickly filtered directly into the −10° ethereal diazomethane. Ether rinses are used to finish the transfer. The vacuum is replaced by the argon line and the reaction is allowed to warm to 0° and is kept at 0° for one hour. The flask is then stoppered, fitted with a balloon and refrigerated overnight.

The reaction mixture is next rinsed with 400 ml. each of 3% aqueous acetic acid, water, saturated sodium bicarbonate, water, and brine, dried (MgSO$_4$) and concentrated in vacuo. The crude product is recrystallized from ether-petroleum ether to give 17.2 g. of [(S)-1-chloro-5-methyl-2-oxo-3-hexyl]carbamic acid, 1,1-dimethylethyl ester; m.p. 87°–89°; $[\alpha]_D = -51.2°$ (c=1, methylene chloride).

Calculated for C$_{12}$H$_{21}$N$_3$O$_3$: C, 56.45; H, 8.29; N, 16.46, Found: C, 56.13; H, 8.31; N, 16.39.

(d) N-[(S)-3-[[(1,1-Dimethylethoxy)carbonyl]amino]-5-methyl-2-oxohexyl]-L-leucine, 2-(trimethylsilyl)ethyl ester A solution of [(S)-1-chloro-5-methyl-2-oxo-3-hexyl]carbamic acid, 1,1-dimethylethyl ester (3.55 g., 13.5 mmole) in dimethylformamide (18 ml.) is added, in one portion, to a mixture of L-leucine, 2-(trimethylsilyl)ethyl ester (5.47 g., 23.6 mmole), sodium iodide (1.06 g., 7.1 mmole), and sodium bicarbonate (2.0 g., 23.6 mmole) in dimethylformamide (18 ml.). The reaction, under an atmosphere of nitrogen, is stirred at ambient temperature overnight, then diluted with 500 ml. of 1:1 ethyl acetate:ether and washed with 100 ml. portions of water, 5% sodium bicarbonate, water, and brine, dried (MgSO$_4$) and concentrated in vacuo to give 7.8 g. of crude product. Flash chromatography on 85 g. of LPS-1 silica gel eluting with 10:1 hexane:ethyl acetate yields 5.0 g. of N-[(S)-3-[[(1,1-dimethylethoxy)carbonyl]amino]-5-methyl-2-oxohexyl]-L-leucine, 2-(trimethylsilyl)ethyl ester as an oil; $[\alpha]_D = -15.5°$ (c=1, chloroform). TLC (silica gel; 6:1 hexane:ethyl acetate) $R_f = 0.11$.

(e)
N-[(S)-3-[[(1,1-Dimethylethoxy)carbonyl]amino]-5-methyl-2-hydroxyhexyl]-L-leucine, 2-(trimethylsilyl)ethyl ester Sodium borohydride (2.1 g., 54.5 mmole) is added to a solution of N-[(S)-3-[[(1,1-dimethylethoxy)carbonyl]amino]-5-methyl-2-oxohexyl]-L-leucine, 2-(trimethylsilyl)ethyl ester (5.0 g., 10.9 mmole) in a mixture of tetrahydrofuran (150 ml.) and water (50 ml.) cooled to an ice-water bath. After 5 minutes the reaction is poured into water (300 ml.) and extracted with ethyl acetate (600 ml.). The organic extract is rinsed further with water and brine, dried (MgSO$_4$) and concentrated in vacuo to yield 4.7 g. of crude product. Flash chromatography on 140 g. of LPS-1 silica gel eluting with 10:1 petroleum ether:acetone yields 3.5 g. of N-[(S)-3-[[(1,1-dimethylethoxy)carbonyl]amino]-5-methyl-2-hydroxyhexyl]-L-leucine, 2-(trimethylsilyl)ethyl ester as an oil; $[\alpha]_D = -27.8°$; (c=1, chloroform). TLC (silica gel; 10:1 petroleum ether:acetone) $R_f = 0.20$.

(f) (2R,3S)- and (2S,3S)-N-[3-[[(1,1-Dimethylethoxy)carbonyl]amino]-5-methyl-2-hydroxyhexyl]-N-[(phenylmethoxy)carbonyl]-L-leucine, 2-(trimethylsilyl)ethyl ester A mixture of N[(S)-3-[[(1,1-dimethylethoxy)carbonyl]amino]-5-methyl-2-hydroxyhexyl]-L-leucine, 2-(trimethylsilyl)ethyl ester (3.5 g., 7.6 mmole) and N-[(phenylmethoxy)carbonyloxy]succinimide (2.8 g., 11.4 mmole) in dry tetrahydrofuran (1.35 ml.) is stirred under nitrogen in a stoppered flask at ambient temperature for 48 hours, then diluted with 100 ml. of ether and rinsed with water and brine, dried (MgSO$_4$) and concentrated in vacuo to give 5.6 g. of crude product. The mixture is flash filtered through 60 g. of LPS-1 silica gel eluting with 20:1 petroleum ether:acetone then separated on a Waters Prep 500 LC using two columns eluted with 25:1 petroleum ether:acetone (250 ml./min., 200 ml. fractions). Homogeneous fractions of the first isomer eluted are pooled to give 1.53 g. of (2S,3S)-N-[3-[[(1,1-dimethylethoxy)carbonyl]amino]-5-methyl-2-hydroxyhexyl]-N-[(phenylmethoxy)carbonyl]-L-leucine, 2-(trimethylsilyl)ethyl ester; $[\alpha]_D = -57.4°$ (c=1, chloroform). TLC (silica gel, 10:1 petroleum ether:acetone) $R_f = 0.24$.

Anal. calc'd. for $C_{31}H_{54}N_2O_7Si$: C, 62.59; H, 9.15; N, 4.71, Found: C, 62.57; H, 8.87; N, 4.99.

After collecting 132 mg. of a mixture fraction, 1.72 g. of pure (2R,3S)-N-[3-[[(1,1-dimethylethoxy)carbonyl]amino]-5-methyl-2-hydroxyhexyl]-N-[(phenylmethoxy)carbonyl]-L-leucine, 2-(trimethylsilyl)ethyl ester is obtained as an oil; $[\alpha]_D = -25.2°$ (c=1, chloroform). TLC (silica gel; 10:1 petroleum ether:acetone) $R_f = 0.21$.

Anal. calc'd. for $C_{31}H_{54}N_2O_7Si$: C, 62.59; H, 9.15; N, 4.71, Found: C, 62.29; H, 9.28; N, 4.62.

(g)
(2R,3S)-N-[[3-[(1,1-Dimethylethoxy)carbonyl]-2,2-dimethyl-4-(2-methylpropyl)oxazolidin-5-yl]methyl]-N-[(phenylmethoxy)carbonyl]-L-leucine, 2-(trimethylsilyl)ethyl ester The (2R,3S) isomer product from part (f) (2.42 g., 4.1 mmole) is dissolved in 72 ml. of dry methylene chloride and treated with 2-methoxypropene (5.9 g., 82 mmole), followed by pyridinium-p-toluenesulfonic acid (0.206 g., 0.802 mmole). The reaction is stirred under nitrogen at room temperature for one hour and then diluted with ether (500 ml.) and rinsed with water and brine, dried (MgSO$_4$), and concentrated in vacuo to give 3.1 g. of crude product. Chromatography on a Waters Prep 500 LC using two columns eluted with 35:1 petroleum ether:acetone (250 ml./min., 125 ml. fractions) yields 2.2 g. of (2R,3S)-N-[[3-[(1,1-dimethylethoxy)carbonyl]-2,2-dimethyl-4-(2-methylpropyl)oxazolidin-5-yl]methyl]-N-[(phenylmethoxy)carbonyl]-L-leucine, 2-(trimethylsilyl)ethyl ester as an oil; $[\alpha]_D = -4.3°$ (c=1, chloroform). TLC (silica gel, 15:1 petroleum ether:acetone) $R_f = 0.44$.

Anal. calc'd. for $C_{34}H_{58}N_2O_7Si$: C, 64.32; H, 9.21; N, 4.41, Found: C, 64.39; H, 9.40; N, 4.25.

(h)
(2R,3S)-N-[N-[[3-[(1,1-Dimethylethoxy)carbonyl]-L-leucyl]-2,2-dimethyl-4-(2-methylpropyl)oxazolidin-5-yl]methyl]-N-[(phenylmethoxy)carbonyl]-L-valine, methyl ester To a solution of the 2-(trimethylsilyl)ethyl ester product from part (g) (2.2 g., 3.46 mmole) in dimethylformamide (26 ml.) under nitrogen at room temperature is added tetra n-butyl ammonium fluoride trihydrate (2.2 g., 6.92 mmole). After 15 minutes, the reaction is diluted with 200 ml. of 1:1 ether:ethyl acetate and rinsed with three 75 ml. portions of water, rinsed with brine, and dried (MgSO$_4$). Removal of solvents in vacuo yields 1.85 g. of the carboxylic acid intermediate. TLC (silica gel, 20:1:1, chloroform:methanol:acetic acid) $R_f = 0.64$.

This crude carboxylic acid material (3.46 mmole) is dissolved in 30 ml. of tetrahydrofuran under nitrogen. The solution is cooled in an ice bath and treated with L-valine, methyl ester, monohydrochloride (580 mg., 3.46 mmole), hydroxybenzotriazole hydrate (530 mg., 3.46 mmole), and finally, dicyclohexylcarbodiimide (749 mg., 3.63 mmole) followed by N-methylmorpholine (350 mg., 3.46 mmole). The reaction mixture is allowed to warm to room temperature overnight, then filtered and taken up in 200 ml. of 1:1 ethyl acetate:ether. The organic solution is rinsed with 60 ml. portions of 5% potassium bisulfate, water, saturated sodium bicarbonate, and brine, dried (MgSO$_4$), and concentrated in vacuo to give 2.4 g. of crude product. Flash chromatography on 120 g. of LPS-1 silica gel eluting with 20:1 petroleum ether:acetone gives 1.9 g. of (2R,3S)-N-[N-[[3-[(1,1-dimethylethoxy)carbonyl]-2,2-dimethyl-4-(2-methylpropyl)oxazolidin-5-yl]methyl]-N-[(phenylmethoxy)carbonyl]-L-leucyl]-L-valine, methyl ester; $[\alpha]_D = +10.4°$ (c=1, chloroform). TLC (silica gel; 15:1 petroleum ether:acetone) $R_f = 0.08$.

(i) (2R,3S)-N-[N-[3-[[N-[(1,1-Dimethylethoxy)carbonyl]-3-[(phenylmethoxy)methyl]-L-histidyl]amino]-2-hydroxy-5-methylhexyl][(phenylmethoxy)carbonyl]-L-leucyl]-L-valine, methyl ester A solution of the methyl ester product from part (h) (1.8 g., 2.78 mmole) in methylene chloride (18 ml.) is cooled to 0° and treated with 9 ml. of trifluoroacetic acid. The cooling bath is removed and the reaction is stirred for one hour. It is then concentrated in vacuo and treated with 12 ml. of tetrahydrofuran and 6 ml. of 1N aqueous hydrochloric acid. After one hour, the reaction mixture is treated with 75 ml. of saturated sodium bicarbonate solution and 75 ml. of chloroform. The basic aqueous layer is further extracted with another 75 ml. of chloroform and the combined organic extracts are rinsed with brine, dried (MgSO$_4$), and concentrated in vacuo to give 1.4 g. of crude aminoalcohol. TLC (silica gel; 10:1 chloroform:methanol) R$_f$=0.31.

The above aminoalcohol (2.78 mmole) is dissolved in tetrahydrofuran (25 ml.) to which is added hydroxybenzotriazole hydrate (425 mg., 2.78 mmole) and 3-[(phenylmethoxy)methyl]-1-[(phenylmethoxy)carbonyl]-L-histidine (1.04 g., 2.78 mmole). The reaction mixture is cooled in an ice bath, treated with dicyclohexylcarbodiimide (602 mg., 2.92 mmole) and allowed to warm to room temperature overnight under nitrogen. The reaction is then diluted with 200 ml. of 4:1 ethyl acetate:ether, filtered, and rinsed with 50 ml. portions of 5% potassium bisulfate, water, saturated sodium bicarbonate, water, and brine, dried (MgSO$_4$), and concentrated in vacuo to give 2.3 g. of crude product. Chromatography on a Waters Prep 500 LC using two columns eluted with 40:1 chloroform:methanol (250 ml./min., 125 ml. fractions) to give 1.9 g. of (2R,3S)-N-[N-[3-[[N-[(1,1-dimethylethoxy)carbonyl]-3-[(phenylmethoxy)methyl]-L-histidyl]amino]-2-hydroxy-5-methylhexyl][(phenylmethoxy)carbonyl]-L-leucyl]-L-valine, methyl ester as a glassy solid; m.p. 62°–67°; $[\alpha]_D$= −22.4° (c=1, chloroform). TLC (silica gel; 20:1 chloroform:methanol) R$_f$=0.34.

Anal. calc'd. for C$_{46}$H$_{86}$N$_6$O$_{10}$.0.6H$_2$O: C, 63.08; H, 7.96; N, 9.60, Found: C, 63.14; H, 7.89; N, 9.20.

(j) (2R,3S)-N-[N-[3-(L-Histidylamino)-2-hydroxy-5-methylhexyl]-L-leucyl]-L-valine, methyl ester, hydrochloride (1:3.1)

A solution of the methyl ester product from part (i) (606 mg., 0.7 mmole) in 14 ml. of 4:1 acetic acid:water containing 4 equivalents of hydrochloric acid (2.8 mmole) is treated with 200 mg. of 10% palladium on carbon catalyst. The reaction mixture is shaken on a Parr apparatus overnight at 50 psi of hydrogen at room temperature. The mixture is converted to the corresponding acetate salts on an AG 1-X2 (10 ml. column bed run in 8:1, water:methanol). The lyophilized mixture of acetate salts is then chromatographed on a 160 ml. HP-20 column gradient eluted from 1.5 l. of 5:95:0.5 methanol:water:acetic acid to 1.5 l. of 70:30:0.2 methanol:water:acetic acid (flow rate 2.5 ml./min., 10 ml. fraction sizes). Homogeneous fractions of the first material eluted yield 225 mg. of (2R,3S)-N-[N-[3-(L-histidylamino)-2-hydroxy-5-methylhexyl]-L-leucyl]-L-valine, methyl ester, triacetate salt.

This triacetate salt is converted to the trihydrochloride salt on an AG 1-X2 (Cl$^-$) column, lyophilized and precipitated from methanol-ether. The resulting slightly yellow solid is thoroughly dried at high vacuum to remove traces of ether and yields 160 mg. of (2R,3S)-N-[N-[3-(L-histidylamino)-2-hydroxy-5-methylhexyl]-L-leucyl]-L-valine, methyl ester, hydrochloide (1:3.1) as a slightly off-white powder; m.p. 182°–232° (dec.); $[\alpha]_D$= −15° (c=0.5, methanol). TLC (silica gel; 5:1:1:1 n-butanol:pyridine:acetic acid:water) R$_f$=0.63.

Anal. calc'd. for C$_{25}$H$_{46}$N$_6$O$_5$.3.1HCl.1.7H$_2$O: C, 45.88; H, 8.09; N, 12.84; Cl. 16.80, Found: C, 45.83; H, 7.73; N, 12.51; Cl, 16.81.

EXAMPLE 2

(2R,3S)-N-[N-[3-[[N-[(1,1-Dimethylethoxy)carbonyl]-L-histidyl]amino]-2-hydroxy-5-methylhexyl]-L-leucyl]-L-valine, methyl ester, acetate salt (1:1)

Pooling of the homogeneous fractions of the second component to yield from the HP-20 column in Example 1 (j) yields 144 mg. of (2R,3S)-N-[N-[3-[[N-[(1,1-dimethylethoxy)carbonyl]-L-histidyl]amino]-2-hydroxy-5-methylhexyl]-L-leucyl]-L-valine, methyl ester, acetate salt (1:1); m.p. 66°–77°; $[\alpha]_D$ = −31.6° (c=0.5, methanol). TLC (silica gel; 90:20:2.5:1 chloroform:methanol:water:acetic acid) R$_f$=0.26.

Anal. calc'd. for C$_{30}$H$_{54}$N$_6$O$_7$.C$_2$H$_4$O$_2$.0.4H$_2$O: C, 56.68; H, 8.74; N, 12.40, Found: C, 56.54; H, 8.67; N, 12.77.

EXAMPLE 3

(2S,3S)-N-[N-[3-[[N-[(1,1-Dimethylethoxy)carbonyl]-L-histidyl]amino]-2-hydroxy-5-methylhexyl]-L-leucyl]-L-valine, methyl ester

(a) (2S,3S)-N-[[3-[(1,1-Dimethylethoxy)carbonyl]-2,2-dimethyl-4-(2-methylpropyl)oxazolidin-5-yl]methyl]-N-[(phenylmethoxy)carbonyl]-L-leucine, 2-(trimethylsilyl)ethyl ester 2-Methoxypropene (3.49 g., 48.4 mmole) is added to a solution of (2S,3S)-N-[3-[[(1,1-dimethylethoxy)carbonyl]amino]-5-methyl-2-hydroxyhexyl]-N-[(phenylmethoxy)carbonyl]-L-leucine, 2-(trimethylsilyl)ethyl ester (1.44 g., 2.42 mmole) [prepared in Example 1(f)] in dry methylene chloride (42 ml.) followed by the addition of pyridine-p-toluenesulfonic acid (0.12 g., 0.48 mmole). The reaction mixture is stirred at ambient temperature under nitrogen for 45 minutes, then diluted with ether (350 ml.), rinsed with water and brine, dried (MgSO$_4$), and concentrated in vacuo to give 2.0 g. of crude product. Flash chromatography on 113 g. of LPS-1 silica gel eluting with a gradient of from 100:1 to 25:1 petroleum ether:acetone yields 1.46 g. of (2S,3S)-N-[[3-[(1,1-dimethylethoxy)carbonyl]-2,2-dimethyl-4-(2-methylpropyl)oxazolidin-5-yl]methyl]-N-[(phenylmethoxy)carbonyl]-L-leucine, 2-(trimethylsilyl)ethyl ester as an oil; $[\alpha]_D$= −19.6° (c=1, chloroform). TLC (silica gel, 10:1 petroleum ether:acetone) R$_f$=0.53.

Anal. calc'd. for C$_{34}$H$_{58}$N$_2$O$_7$Si: C, 64.32; H, 9.21; N, 4.41, Found: C, 64.60; H, 9.19; N, 4.24.

(b) (2S,3S)-N-[N-[[3-[(1,1-Dimethylethoxy)carbonyl]-2,2-dimethyl-4-(2-methylpropyl)oxazolidin-5-yl]methyl]-N-[(phenylmethoxy)carbonyl]-L-leucyl]-L-valine, methyl ester To a solution of the 2-(trimethylsilyl)ethyl ester product from part (a) (1.6 g., 2.52 mmole) in dimethylformamide (19 ml.) is added tetra n-butyl ammonium fluoride trihydrate (1.6 g., 5.04 mmole). After 15 minutes, the reaction is diluted with 200 ml. of 1:1 ethyl acetate:ether. The organic extract is rinsed with water and brine, dried (MgSO$_4$), and concentrated in vacuo to give 1.4 g. of crude carboxylic acid intermediate.

This crude carboxylic acid (2.52 mmole) is dissolved in tetrahydrofuran (22 ml.). The solution is cooled in an ice bath under nitrogen and treated with hydroxybenzotriazole hydrate (0.385 g.) and L-valine, methyl ester, monohydrochloride (0.422 g., 2.52 mmole). Dicyclohexylcarbodiimide (0.547 g., 2.65 mmole) is added followed by N-methylmorpholine (0.255 g., 2.52 mmole). The reaction mixture is allowed to warm to room temperature overnight, then filtered, and taken up in 180 ml. of 2:1 ethyl acetate:ether. The organic solution is rinsed with 5% potassium bisulfate, water, saturated sodium bicarbonate, water, and brine, dried (MgSO$_4$), and concentrated in vacuo to give 1.8 g. of crude product. Flash chromatography on 90 g. of LPS-1 silica gel eluting with 15:1 petroleum ether-acetone gives 1.35 g. of (2S,3S)-N-[N-[[3-[(1,1-dimethylethoxy)carbonyl]-2,2-dimethyl-4-(2-methylpropyl)oxazolidin-5-yl]methyl]-N-[(phenylmethoxy)carbonyl]-L-leucyl]-L-valine, methyl ester $[\alpha]_D = -55.1°$ (c=1, chloroform). TLC (silica gel; 10:1 petroleum ether:acetone) R$_f$=0.13.

Anal. Calc'd. for C$_{35}$H$_{57}$N$_3$O$_8$: C, 64.89; H, 8.87; N, 6.49, Found: C, 64.88; H, 8.98; N, 6.34.

(c)
(2S,3S)-N-[N-[3-[[N-[(1,1-Dimethylethoxy)carbonyl]-3-[(phenylmethoxy)methyl]-L-histidyl]amino]-2-hydroxy-5-methylhexyl]-[(phenylmethoxy)carbonyl]-L-leucyl]-L-valine, methyl ester A solution of the methyl ester product from part (b) (585 mg., 0.903 mmole) in dry methylene chloride (6 ml.) is cooled in an ice-water bath under argon and treated with 3 ml. of trifluoroacetic acid. The cooling bath is removed and after one hour the reaction mixture is concentrated in vacuo to an oil. This oil is dissolved in tetrahydrofuran (4 ml.) and then treated with 1N aqueous hydrochloric acid (2 ml.). The resulting mixture is stirred for 5 hours at room temperature then basified with saturated sodium bicarbonate solution (25 ml.). The mixture is extracted with two 25 ml. portions of chloroform. The organic extract is rinsed with brine, dried (MgSO$_4$), and concentrated in vacuo to give 440 mg. of crude aminoalcohol product. TLC (silica gel; 9:1 chloroform:methanol) R$_f$=0.28.

This aminoalcohol (0.867 mmole) is dissolved in tetrahydrofuran (8 ml.). To the resulting solution is added hydroxybenzotriazole hydrate (133 mg., 0.867 mmole) and 3-[(phenylmethoxy)methyl]-1-[(phenylmethoxy)carbonyl]-L-histidine (325 mg., 0.867 mmole). The mixture is cooled in an ice-bath under argon and treated with dicyclohexylcarbodiimide (188 mg., 0.910 mmole). The reaction is allowed to warm to room temperature overnight, then filtered and taken up in 6:1 ethyl acetate:ether. The solution is rinsed with 15 ml. portions of 5% potassium bisulfate, water, saturated sodium bicarbonate, water, and brine, dried (MgSO$_4$), and concentrated in vacuo to give 758 mg. of crude product. Flash chromatography on 40 g. of LPS-1 silica gel eluting with 20:1 chloroform:methanol give 686 mg. of (2S,3S)-N-[N-[3-[[N-([(1,1-dimethylethoxy)carbonyl]-3-[(phenylmethoxy)methyl]-L-histidyl]amino]-2-hydroxy-5-methylhexyl]-[(phenylmethoxy)carbonyl]-L-leucyl]-L-valine, methyl ester as a glassy solid; m.p. 53°–60°; $[\alpha]_D = -55.2°$ (c=1, chloroform). TLC (silica gel; 20:1 chloroform:methanol) R$_f$=0.13.

Anal. calc'd. for C$_{46}$H$_{68}$N$_6$O$_{10}$.1H$_2$O: C, 62.56; H, 7.99; N, 9.52, Found: C, 62.51; H, 7.98; N, 9.39.

(d)
(2S,3S)-N-[N-[3-[[N-[(1,1-dimethylethoxy)carbonyl]-L-histidyl]amino]-2-hydroxy-5-methylhexyl]-L-leucyl]-L-valine, methyl ester To a solution of the methyl ester product from part (c) (605 mg., 0.7 mmole) in 12 ml. of 4:0.8:0.2 acetic acid:water:dimethylformamide containing 2.2 equivalents of hydrochloric acid is added 280 mg. of 10% palladium on carbon catalyst. The mixture is shaken on a Parr apparatus at 50 psi of hydrogen for 18 hours, then filtered and concentrated in vacuo to 560 mg. of crude product. Repeated HP-20 gradient chromatographies using methanol:water:dilute acetic acid finally yield 290 mg. of purified product. A final flash chromatography using 25 g. of LPS-1 silica gel eluting with 100:25:2.5:1 chloroform:methanol:water:acetic acid yields 212 mg. of (2S,3S)-N-[N-[3-[[N-[(1,1-dimethylethoxy)carbonyl]-L-histidyl]amino]-2-hydroxy-5-methylhexyl]-L-leucyl]-L-valine, methyl ester; m.p. 73°–82°; $[\alpha]_D = -40.2°$ (c=0.5, methanol). TLC (silica gel; 90:20:2.5:1 chloroform:methanol:water:acetic acid) R$_f$=0.34.

Anal. calc'd. for C$_{30}$H$_{54}$N$_6$O$_7$.1.2H$_2$O: C, 56.97; H, 8.99; N, 13.29, Found: C, 56.94; H, 8.87; N, 13.14.

EXAMPLE 4

(2S,3S)-N-[N-[3-(1-Histidylamino)-2-hydroxy-5-methylhexyl]-L-leucyl]-L-valine, methyl ester, hydrochloride (1:3)

A solution of (2S,3S)-N-[N-[[N--[(1,1-dimethylethoxy)carbonyl]-L-histidinyl]amino]-2-hydroxy-5-methylhexyl]-L-leucyl]-L-valine, methyl ester (108 mg., 0.17 mmole) in distilled trifluoroacetic acid (15 ml.) is blanketed with nitrogen, stoppered, and stirred at room temperature. After one hour, the reaction is concentrated in vacuo to give 193 mg. of crude product. This is combined with 10 mg. from a previous run and the entire 203 mg. is chromatographed on 6.4 ml. (5.5 eq.) of AG 1-X2 (Cl$^-$) resin eluting with water. Lyophilization gives 121 mg. of partially purified product. This 121 mg. is resubjected to 15 ml. of trifluoroacetic acid for one hour and then concentrated in vacuo and lyophilized. Chromatography is performed on a 35 ml. column of HP-20 resin packed in 96:2:2 water:1N hydrochloric acid:methanol and eluted with a gradient from 150 ml. of 96:2:2 to 150 ml. of 58:2:40 water:1N hydrochloric acid:methanol. Pooling of homogeneous product containing fractions gives 92 mg. of (2S,3)-N-[N-[3-(L-histidylamino)-2-hydroxy-5-methylhexyl]-L-leucyl]-L-valine, methyl ester, hydrochloride (1:3); m.p. 180°–250°; $[\alpha]_D = -25.8°$ (c=0.5, methanol). TLC (silica gel 5:1:1:1 n-butanol:pyridine:acetic acid:water) R$_f$=0.67.

Anal. calc'd. for C$_{25}$H$_{46}$N$_6$O$_5$.3HCl.2.3H$_2$O: C, 45.39; H, 8.17; N, 12.71; Cl, 16.08, Found: C, 45.36; H, 7.91; N, 12.70; Cl, 16.04.

EXAMPLE 5

(2S,3S)-N-[N-[3-[[N-[N-[(1,1-dimethylethoxy)carbonyl]-L-phenylalanyl]-L-histidyl]amino]-2-hydroxy-5-methylhexyl]-L-leucyl]-L-valine, methyl ester, monoacetate salt (a)

(2S,3S)-N-[N-[3-[[N-[N-[(1,1-dimethylethoxy)carbonyl]-L-phenylalanyl]-3-[(phenylmethoxy)methyl]-L-histidyl]amino]-2-hydroxy-5-methylhexyl]-L-leucyl]-L-valine, methyl ester A solution of (2S,3S)-N-[N-[3-[[N-[(1,1-dimethylethoxy)carbonyl]-3-[(phenylmethoxy)methyl]-L-histidyl]amino]-2-hydroxy-5-methylhexyl]-[(phenylmethoxy)carbonyl]-L-leucyl]-L-valine, methyl ester (1.20 g., 1.39 mmole) [prepared as set forth in Example 3(c)] in ethyl acetate (20 ml.) is cooled in an ice-water bath under nitrogen and saturated with HCl gas. The bath is removed and the stoppered reaction is kept at room temperature for 80 minutes, then concentrated in vacuo and triturated with ether. The crude bis-hydrochloride product weighs 1.02 g.

A solution of this material (1.02 g., 1.22 mmole), N-[(1,1-dimethylethoxy)carbonyl]-L-phenylalanine (0.323 g., 1.22 mmole), and hydroxybenzotriazole hydrate (0.181 g., 1.34 mmole) in dimethylformamide (14 ml.) is cooled in an ice-water bath under nitrogen and treated with dicyclohexylcarbodiimide (0.264 g., 1.28 mmole) followed by N-methylmorpholine (0.246 g., 1.28 mmole). The reaction is allowed to come to room temperature overnight, then diluted with 30 ml. of ethyl acetate, filtered, diluted further with 60 ml. of ethyl acetate and 25 ml. of ether. The resulting mixture is rinsed with 20 ml. portions of 5% aqueous potassium bisulfate, water, saturated sodium bicarbonate, water, and brine, dried (MgSO$_4$), and concentrated in vacuo to 1.35 g. of crude product. Flash chromatography on 80 g. of LPS-1 silica gel gradient eluted with from 2:1 chloroform:ethyl acetate to 16:1 chloroform:methanol is used. Pooling of homogeneous product containing fractions gives 820 mg. of (2S,3S)-N-[N-[3-[[N-[N[(1,1-dimethylethoxy)carbonyl]-L-phenylalanyl]-3-[(phenylmethoxy)methyl]-L-histidyl]amino]-2-hydroxy-5-methylhexyl]-L-leucyl]-L-valine, methyl ester; m.p. 71°–81°; [α]$_D$=33.1° (c=1, chloroform). TLC (silica gel; 12:1 chloroform:methanol) R$_f$=0.22.

(b)

(2S,3S)-N-[N-[3-[[N-[N-[(1,1-Dimethylethoxy)carbonyl]-L-phenylalanyl]L-histidyl]amino]-2-hydroxy-5-methylhexyl]-L-leucyl]-L-valine, methyl ester, monoacetate salt A mixture of the methyl ester product from part (a) (500 mg., 0.490 mmole), 20% palladium hydroxide on carbon catalyst (150 mg.), and 1N aqueous hydrochloric acid (1.08 ml.) in 24 ml. of 5:1 methanol:water is shaken on a Parr apparatus under 50 psi of hydrogen for 16 hours. The reaction is filtered, concentrated in vacuo, and flash chromatographed on 40 g. of LPS-1 silica gel eluting with 100:20:2.5:1 chloroform:methanol:water:acetic acid. Product containing fractions are pooled and triturated with ether to give 271 mg. of (2S,3S)-N-[N-[3-[[N-[N-[(1,1-dimethylethoxy)carbonyl]-L-phenylalanyl]-L-histidyl]amino]-2-hydroxy-5-methylhexyl]-L-leucyl]-L-valine, methyl ester, monoacetate salt; m.p. 81°–93°; [α]$_D$=−27.8° (c=0.5, methanol). TLC (silica gel; 100:20:2.5:1 chloroform:methanol:water:acetic acid) R$_f$=0.52.

Anal. calc'd. for C$_{39}$H$_{63}$N$_7$O$_8$·C$_2$H$_4$O$_2$·0.6H$_2$O: C, 59.41; H, 8.29; N, 11.83, Found: C, 59.43; H, 8.38; N, 11.55.

EXAMPLE 6

(2R,3S)-N-[N-[3-[[N-[N-[(1,1-Dimethylethoxy)carbonyl]-L-phenylalanyl]-L-histidyl]amino]-2-hydroxy-5-methylhexyl]-L-leucyl]-L-valine, methyl ester, monoacetate salt (a)

(2R,3S)-N-[N-[3-[[N-[N-[(1,1-dimethylethoxy)carbonyl]-L-phenylalanyl]-3-[(phenylmethoxy)methyl]-L-histidyl]amino]-2-hydroxy-5-methylhexyl]-L-leucyl]-L-valine, methyl ester A solution of (2R,3S)-N-[N-[3-[[N-[(1,1-dimethylethoxy)carbonyl]-3-[(phenylmethoxy)methyl]-L-histidyl]amino]-2-hydroxy-5-methylhexyl]-[(phenylmethoxy)carbonyl]-L-leucyl]-L-valine, methyl ester (1.23 g., 1.42 mmole) [prepared as set forth in Example 1(i)] in ethyl acetate (20 ml.) is cooled in an ice-water bath under argon and saturated with dry HCl. The bath is removed and after 40 minutes the reaction mixture is concentrated in vacuo to a glassy substance which is triturated with ether. The crude bis-hydrochloride product obtained weighs 1.08 g.

A solution of this material (1.08 g., 1.29 mmole), N-[(1,1-dimethylethoxy)carbonyl]-L-phenylalanine (0.342 g., 1.29 mmole), and hydroxybenzotriazole hydrate (0.192 g., 1.42 mmole) in dimethylformamide (15 ml.) is cooled in an ice-water bath under argon and treated with dicyclohexylcarbodiimide (0.279 g., 1.35 mmole) followed by N-methylmorpholine (0.261 g., 2.58 mmole). The reaction is allowed to warm to room temperature overnight, then diluted with 30 ml. of ethyl acetate, chilled in an ice-bath for 15 minutes, and then filtered. The extract is next treated with 25 ml. of ether and the organic solution is rinsed with 20 ml. portions of 5% potassium bisulfate, water, saturated sodium bicarbonate, water, and brine, dried (MgSO$_4$), and concentrated in vacuo to give 1.43 g. of crude product. Flash chromatography on 77 g. of LPS-1 silica gel packed and initially eluted with 2:1 chloroform:ethyl acetate (150 ml.) followed by a gradient from 400 ml. of 2:1 chloroform:ethyl acetate to 16:1 chloroform:methanol gives 1.09 g. of (2R,3S)-N-[N-[3-[[N-[N-[(1,1-dimethylethoxy)carbonyl]-L-phenylalanyl]-3-[(phenylmethoxy)methyl]-L-histidyl]-amino]-2-hydroxy-5-methylhexyl]-L-leucyl]-L-valine, methyl ester as a homogeneous product; m.p. 73°–80°; [α]$_D$=−18.1° (c=1, chloroform). TLC (silica gel; 12:1 chloroform:methanol) R$_f$=0.43.

(b)

(2R,3S)-N-[N-[3-[[N-[N-[(1,1-dimethylethoxy)carbonyl]-L-phenylalanyl]-L-histidyl]amino]-2-hydroxy-5-methylhexyl]-L-leucyl]-L-valine, methyl ester, monoacetate salt To a solution of the methyl ester product form part (a) (500 mg., 0.490 mmole) in a mixture of 20 ml. of methanol and 4 ml. of water is added 1N aqueous hydrochloric acid (1.08 ml.) and 20% palladium hydroxide on carbon catalyst (150 mg.). The reaction mixture is hydrogenated under 50 psi of hydrogen on a Parr apparatus for 15 hours at room temperature, then filtered and concentrated in vacuo to 400 mg. of crude product. Flash chromatography on 45 g. of LPS-1 silica gel eluting with 100:20:2.5:1 chloroform:methanol:water:acetic acid yields 310 mg. of purified product. Trituration with ether followed by drying (vacuum pump) at room temperature for about 36 hours yields 300 mg. of (2R,3S)-N-[N-[3-[[N-[N-[(1,1-dimethylethoxy)carbonyl]-L-phenylalanyl]-L-histidyl]amino]-2-hydroxy-5-methylhexyl]-L-leucyl]-L-valine, methyl ester, monoacetate salt; m.p. 79°-95°; $[\alpha]_D = -21.2°$ (c=0.5, methanol). TLC (silica gel; 100:20:2.5:1 chloroform:methanol:water:acetic acid) $R_f=0.44$.

Anal. calc'd. for $C_{39}H_{63}N_7O_8 \cdot C_2H_4O_2 \cdot 1.0H_2O$: C, 58.90; H, 8.32; N, 11.73, Found: C, 58.83; H, 8.22; N, 11.68.

EXAMPLE 7

(2S,3S)-N-[N-[2-Hydroxy-5-methyl-3-[[N-(L-phenylalanyl)-L-histidyl]amino]butyl]-L-leucyl]-L-valine, methyl ester, trihydrochloride Trifluoroacetic acid (15 ml.) is cooled in an ice-bath under nitrogen, then treated with (2S,3S)-N-[N-[3-[[N-[N-[(1,1-dimethylethoxy)carbonyl]-L-phenylalanyl]-L-histidyl]amino]-2-hydroxy-5-methylhexyl]-L-leucyl]-L-valine, methyl ester, monoacetate salt (1.32 mg., 0.17 mmole) [prepared as set forth in Example 5]. The ice bath is removed, and the reaction is stirred at ambient temperature under nitrogen. After one hour, the reaction is concentrated in vacuo and lyophilized from water containing 2.5 ml. of 1N aqueous hydrochloric acid (5 eq.) to obtain 128 mg. of the crude trihydrochloride salt. Chromatography is performed on a 35 ml. column of HP-20 resin eluted with a gradient from 150 ml. of 96:2:2 water:1N hydrochloric acid:methanol to 150 ml. of 58:2:40 water:1N hydrochloric acid:methanol. The product containing fractions are pooled and lyophilized to give 70 mg. of partially purified product. Relyophilization from water affords 39 mg. of (2S,3S)-N-[N-[2-hydroxy-5-methyl-3-[[N-(L-phenylalanyl)-L-histidyl]-amino]butyl]-L-leucyl]-L-valine, methyl ester, trihydrochloride; m.p. 188°-220°; $[\alpha]_D = -23.2°$ (c=0.5, methanol). TLC (silica gel; 5:1:1:1 n-butanol:pyridine:acetic acid:water) $R_f=0.76$.

Anal. calc'd. for $C_{34}H_{55}N_7O_6 \cdot 3.1HCl \cdot 3.5H_2O$: C, 48.96; H, 7.87; N, 11.76; Cl, 13.18, Found: C, 49.09; H, 7.53; N, 11.66; Cl, 13.32.

EXAMPLE 8

(2R,3S)-N-[N-[2-Hydroxy-5-methyl-3-[[N-(L-phenylalanyl)-L-histidyl]amino]butyl]-L-leucyl]-L-valine, methyl ester, trihydrochloride Trifluoroacetic acid (11 ml.) is cooled in an ice-bath under nitrogen, then treated with (2R,3S)-N-[N-[3-[[N-[N-[(1,1-dimethylethoxy)carbonyl]-L-phenylalanyl]-L-histidyl]amino]-2-hydroxy-5-methylhexyl]-L-leucyl]-L-valine, methyl ester, monoacetate salt (100 mg., 0.13 mmole) [prepared as set forth in Example 6], and the reaction is stirred cold under nitrogen. After one hour, the reaction is concentrated in vacuo and lyophilized from water containing 2 ml of 1N aqueous hydrochloric acid (5 eq.) to give 104 mg. of crude hydrochloride salt. Chromatography is performed on a 35 ml. column of HP-20 resin eluting with a gradient from 150 ml. of 96:2:2 water:1N hydrochloric acid:methanol to 150 ml. of 54:2:44 water:1N hydrochloric acid:methanol. The product containing fractions are pooled and lyophilized to give 80 mg. of (2R,3S)-N-[N-[2-hydroxy-5-methyl-3-[[N-(L-phenylalanyl)-L-histidyl]amino]butyl]-L-leucyl]-L-valine, methyl ester, trihydrochloride; m.p. 95°-115°; $[\alpha]_D = -11.0$ (c=0.5, methanol). TLC (silica gel; 5:1:1:1 n-butanol:pyridine:acetic acid:water) $R_f=0.61$.

Anal. calc'd. for $C_{34}H_{55}N_7O_6 \cdot 3HCl \cdot 2.5H_2O$: C, 50.25; H, 7.82; N, 12.06; Cl, 13.09, Found: C, 50.25; H, 7.58; N, 12.00; Cl, 12.87.

EXAMPLE 9

N-[N-[(3S)-3-[[N-[N-[(1,1-Dimethylethoxy)carbonyl]-L-phenylalanyl]-L-histidyl]amino]-2-hydroxy-5-methylhexyl]-L-leucyl]-L-phenylalanine, methyl ester, acetic acid salt (1:2)

(a) 3-[(Phenylmethoxy)methyl]-L-histidine, methyl ester, dihydrochloride

N-[(1,1-Dimethylethoxy)carbonyl]-3-[(phenylmethoxy)methyl]-L-histidine, methyl ester, monohydrochloride (7.8 g., 18.3 mmole) [prepared according to the procedure of Brown et al., J.Chem. Soc. Perkins Trans., Vol. 1, p. 2261 (1979)] is suspended in ethyl acetate (140 ml.) under a flow of nitrogen, cooled in an ice-water bath. Dry hydrogen chloride is bubbled in to saturation and the resulting solution is stoppered and kept cold for 20 minutes and then at ambient temperature for 40 minutes. The reaction mixture is then concentrated in vacuo to give 8.4 g. of crude product. Recrystallization from hot isopropanol yields 5.2 g. of 3-[(phenylmethoxy)methyl]-L-histidine, methyl ester, dihydrochloride; m.p. 159°-160°; resolidified at m.p. 209°-210°. $[\alpha]_D = +13.4°$ (c=1.11, methanol).

(b) N-[N-[(1,1-Dimethylethoxy)carbonyl]-L-phenylalanyl]-3-[(phenylmethoxy)methyl]-L-histidine, methyl ester Dicyclohexylcarbodiimide (2.17 g., 10.5 mmole) is added to a mixture of 3-[(phenylmethoxy)methyl]-L-histidine, methyl ester, dihydrochloride (3.62 g., 10 mmole), N-[(1,1-dimethylethoxy)carbonyl]-L-phenylalanine (2.56 g., 10 mmole), and hydroxybenzotriazole hydrate (1.68 g., 11 mmole) in dimethylformamide (70 ml.) cooled in an ice-bath under nitrogen followed by the addition of N-methylmorpholine (2.02 g., 20 mmole). The reaction is allowed to warm to room temperature overnight, then chilled for 15 minutes in an ice-bath after diluting with 200 ml. of ethyl acetate. The cold solution is filtered and the filtrate is washed with three 70 ml. portions of water, saturated sodium bicarbonate and brine, dried (MgSO₄), and concentrated in vacuo to give 4.9 g. of crude product. Flash chromatography on 250 g. of LPS-1 silica gel eluting with 3 column volumes of 1:1 chloroform:ethyl acetate followed by a gradient to 15:1 chloroform:methanol yields 4.2 g. of purified product. Recrystallization from hot ethyl acetate affords 3.7 g. of N-[N-[(1,1-dimethylethoxy)carbonyl]-L-phenylalanyl]-3-[(phenylmethoxy)methyl]-L-histidine, methyl ester; m.p. 165°-166°; $[\alpha]_D = -15.4°$ (c=0.5, methanol). TLC (silica gel); chloroform:methanol 12:1) $R_f=0.40$.

(c) N-[N-[(1,1-Dimethylethoxy)carbonyl]-L-phenylalanyl]-3-[(phenylmethoxy)methyl]-L-histidine 1N Aqueous sodium hydroxide (6.8 ml.) is added to a solution of N-[N-[(1,1-dimethylethoxy)carbonyl]-L-phenylalanyl]-3-[(phenylmethoxy)methyl]-L-histidine, methyl ester (3.3 g., 6.1 mmole) in methanol (18 ml.). After 3 hours, the reaction is diluted with water (42 ml.)

and then concentrated in vacuo to remove most of the methanol. The resulting solution is rinsed with 25 ml. of ether and then acidified to pH of 4.5 using 1N hydrochloric acid. The precipitated solid is filtered, washed with water, and dried in vacuo to give 2.95 g. of N-[N-[(1,1-dimethylethoxy)carbonyl]-L-phenylalanyl]-3-[(phenylmethoxy)methyl]-L-histidine; m.p. 189°-190° (dec.); $[\alpha]_D = -5.7°$ (c=1, dimethylformamide). TLC (silica gel; 2% NH$_4$OH in n-propanol) R$_f$=0.36.

(d)
N-[(S)-3-[[(1,1-Dimethylethoxy)carbonyl]amino]-5-methyl-2-hydroxyhexyl]-N-[(phenylmethoxy)carbonyl]-L-leucine, 2-(trimethylsilyl)ethyl ester A mixture of N[(S)-3-[[(1,1-dimethylethoxy)carbonyl]amino]-5-methyl-2-hydroxyhexyl]-L-leucine, 2-(trimethylsilyl)ethyl ester (3.5 g., 7.6 mmole) and N-[(phenylmethoxy)carbonyloxy]succinimide (2.8 g., 11.4 mmole) in dry tetrahydrofuran (13.5 ml.) is stirred under nitrogen in a stoppered flask at ambient temperature for 48 hours, then diluted with 100 ml. of ether and rinsed with water and brine, dried (MgSO$_4$) and concentrated in vacuo to give 5.6 g. of crude product. The mixture is flash filtered through 60 g. of LPS-1 silica gel eluting with 20:1 petroleum ether:acetone to give 4.3 g. of N-[(S)-3-[[(1,1-dimethylethoxy)carbonyl]amino]-5-methyl-2-hydroxyhexyl]-N-[(phenylmethoxy)carbonyl]-L-leucine, 2-(trimethylsilyl)ethyl ester as a mixture of isomers.

(e)
N-[[(3S)-3-[(1,1-Dimethylethoxy)carbonyl]-2,2-dimethyl-4-(2-methylpropyl)oxazolidin-5-yl]methyl]-N-[(phenylmethoxy)carbonyl]-L-leucine, 2-(trimethylsilyl)ethyl ester N-[(S)-3-[[(1,1-Dimethylethoxy)carbonyl]amino]-methyl-2-hydroxyhexyl]-N-[(phenylmethoxy)carbonyl]-L-leucine, 2-(trimethylsilyl)ethyl ester (1.9 g., 3.2 mmole) is dissolved in dry methylene chloride (7 ml.) and treated with 2-methoxypropene (0.690 g., 9.6 mmole) followed by pyridinium-p-toluenesulfonic acid. The reaction is stirred at room temperature under nitrogen for five hours and then diluted with 500 ml. of ether and rinsed with two 75 ml. portions of water and 75 ml. of brine, dried (MgSO$_4$), and concentrated in vacuo to give the crude product. Flash chromatography on 100 g. of LPS-1 silica gel eluting with a gradient from 100:1 to 25:1 petroleum ether:acetone gives 1.9 g. of N-[[(3S)-3-[(1,1-dimethylethoxy)carbonyl]-2,2-dimethyl-4-(2-methylpropyl)oxazolidin-5-yl]methyl]-N-[(phenylmethoxy)carbonyl]-L-leucine, 2-trimethylsilyl)ethyl ester.

(f)
N-[N-[[(3S)-3-[(1,1-Dimethylethoxy)carbonyl]-2,2-dimethyl-4-(2-methylpropyl)oxazolidin-5-yl]methyl]-N-[(phenylmethoxy)carbonyl]-L-leucyl]-L-phenylalanine, methyl ester A solution of N-[[(3S)-3-[(1,1-dimethylethoxy)carbonyl]-2,2-dimethyl-4-(2-methylpropyl)oxazolidin-5-yl]methyl]-N-[(phenylmethoxy)carbonyl]-L-leucine, 2-(trimethylsilyl)ethyl ester (940 mg., 1.48 mmole) in dimethylformamide (11 ml.) at room temperature under argon is treated with n-tetra butyl ammonium fluoride (934 mg., 2.96 mmole). After 15 minutes, the reaction is worked up by diluting with 50 ml. of ether and 50 ml. of ethyl acetate, rinsed with water (3×25 ml.) and brine, dried (MgSO$_4$), and concentrated in vacuo to give 765 mg. of the free acid intermediate.

A solution of this free acid (375 mg., 0.701 mmole), L-phenylalanine, methyl ester, hydrochloride (151 mg., 0.701 mmole), and hydroxybenzotriazole hydrate (107 mg., 0.701 mmole) in tetrahydrofuran (7 ml.) is cooled in an ice-bath under argon is treated with dicyclohexylcarbodiimide (152 mg., 0.736 mmole) followed by N-methylmorpholine (70.9 mg., 0.701 mmole) dropwise. The reaction is allowed to warm to ambient temperature overnight. Afterward, the reaction is worked up by diluting with ethyl acetate (30 ml.), stirring in an ice-bath for 15 minutes, filtering, and adding an additional 30 ml. of ether. The organic solution is rinsed with 10 ml. portions of 2% potassium bisulfate, water, saturated sodium bicarbonate, and brine, dried (MgSO$_4$), and concentrated in vacuo to yield 480 mg. of crude product. This crude material is purified by flash chromatography on 30 g. of LPS-1 silica gel, packed in petroleum ether, and eluted with a 10:1 mixture of petroleum ether:acetone. The product containing fractions are pooled to give 433 mg. of N-[N-[[(3S)-3-[(1,1-dimethylethoxy)carbonyl]-2,2-dimethyl-4-(2-methylpropyl)oxazolidin-5-yl]methyl]-N-[(phenylmethoxy)carbonyl]-L-leucyl]-L-phenylalanine, methyl ester.

(g)
N-[N-[(3S)-3-[[N-[N-[(1,1-dimethylethoxy)carbonyl]-L-phenylalanyl]-3-[(phenylmethoxy)methyl]-L-histidyl]amino]-2-hydroxy-5-methylhexyl]-N-[(phenylmethoxy)carbonyl]-L-leucyl]-L-phenylalanine, methyl ester A solution of the methyl ester product from part (f) (433 mg., 0.62 mmole) in dry methylene chloride (4 ml.) is cooled in an ice bath under nitrogen and treated with 2 ml. of trifluoroacetic acid. The bath is removed, and after stirring at ambient temperature for one hour, the reaction is concentrated in vacuo. The resulting brown oil is dissolved in 3 ml. of tetrahydrofuran and treated with 1N aqueous hydrochloric acid (1.3 ml., 1.3 mmole), and stirred at room temperature. After 4 hours, the reaction is worked up by diluting with 20 ml. of saturated aqueous sodium bicarbonate, and extracting with chloroform (2×20 ml.). The organic extracts are combined, rinsed with brine, dried (MgSO$_4$), and concentrated in vacuo to 400 mg. of crude free amine.

A solution of this crude free amine (400 mg., about 0.62 mmole), hydroxybenzotriazole hydrate (95 mg., 0.62 mmole), and N-[N-[(1,1-dimethylethoxy)carbonyl]-L-phenylalanyl]-3-[(phenylmethoxy)methyl]-L-histidine (324 mg., 0.62 mmole), from part (c), in dimethylformamide (5 ml.) is cooled in an ice-bath under nitrogen, then treated with dicyclohexylcarbodiimide (135 mg., 0.65 mmole), and the reaction is stoppered and stored under refrigeration overnight. Afterward, the reaction is worked up by diluting with ethyl acetate (40 ml.) and ether (10 ml.), stirring for 45 minutes in an ice bath, filtering, washing the filtrate with 10 ml. portions of 5% aqueous potassium bisulfate, water, saturated aqueous sodium bicarbonate, and brine, dried (MgSO$_4$), and concentrated in vacuo to 650 mg. of crude product. This material is purified by flash chromatography on 40 g. LPS-1 silica gel, packed in 2:1 chloroform:ethyl acetate, and eluting with the following: (1) two column volumes of 2:1 chloroform:ethyl acetate, (2) one column volume of a 50:50 mixture of (2:1, chloroform:ethyl acetate):(30:1, chloroform:methanol), and (3) 30:1 chloroform:methanol. The product containing fractions are pooled to give 500 mg. of N-[N-[(3S)-3-[[N-[N-[(1,1-dimethylethoxy)carbonyl]-L-phenylalanyl]-3-[(phenylmethoxy)methyl]-L-histidyl]amino]-2-hydroxy-5- methylhexyl]-N-[(phenylmethoxy)carbonyl]-L-leucyl]-L-phenylalanine, methyl ester; $[\alpha]_D = -12.6°$ (c=1, chloroform). TLC (silica gel; 20:1 chloroform:methanol) $R_f=0.26$.

(h) N-[N-[(3S)-3-[[N-[N-[(1,1-Dimethylethoxy)carbonyl]-L-phenylalanyl]-L-histidyl]amino]-2-hydroxy-5-methylhexyl]-L-leucyl]-L-phenylalanine, methyl ester, acetic acid salt (1:2)

A solution of the methyl ester product from part (g) (470 mg., 0.44 mmole) in methanol (18 ml.) and water (3.6 ml.) is treated with 1N aqueous hydrochloric acid (0.97 ml., 0.97 mmole) and 20% palladium hydroxide on carbon catalyst (135 mg.). The reaction is subjected to 50 psi of hydrogen on a Parr apparatus overnight. Afterward, an additional 135 mg. of 20% palladium hydroxide on carbon catalyst is added, and the reaction is again subjected to 50 psi of hydrogen on the Parr appatatus. After 6 hours, the reaction is filtered, then concentrated in vacuo, and the residue is partitioned between 100 ml. each of saturated aqueous sodium bicarbonate and chloroform. The organic layer is separated, washed with brine, dried (MgSO$_4$), and concentrated in vacuo to give 510 mg. of crude product. This material is purified by flash chromatography on 51 g. of LPS-1 silica gel, packed and eluted with 100:20:2.5:1 of chloroform:methanol:water:acetic acid. The product containing fractions are pooled and triturated with a few volumes of ether and dried to give 297 mg. of N-[N-[(3S)-3-[[N-[N-[(1,1-dimethylethoxy)carbonyl]-L-phenylalanyl]-L-histidyl]amino]-2-hydroxy-5-methylhexyl]-L-leucyl]-L-phenylalanine, methyl ester, acetic acid salt (1:2); m.p. 70°-82°; $[\alpha]_D = -17.6°$ (c=0.5, methanol). TLC (silica gel, 90:20:2.5:1 chloroform:methanol:water:acetic acid) $R_f=0.47$.

Anal. calc'd. for $C_{43}H_{63}N_7O_8 \cdot 2C_2H_4O_2 \cdot 1H_2O$: C, 59,79; H, 7.79; N, 10.38 Found: C, 59.86; H, 7.66; N, 10.52.

EXAMPLES 10–27

Following the procedures of Examples 1 to 9, the aminoalcohol shown below in Col. I is reacted with the carboxylic acid shown in Col. II to give the product shown in Col. III.

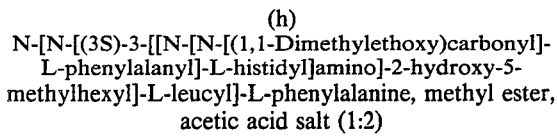

Col. I $$H_2N-\underset{\underset{R_2}{|}}{CH}-\underset{\underset{OH}{|}}{CH}-CH_2-\underset{\underset{R_1}{|}}{N}-\underset{\underset{R_3}{|}}{CH}-\underset{\underset{O}{\|}}{C}-\underset{\underset{R_{12}}{|}}{N}-\underset{\underset{R}{|}}{CH}-\underset{\underset{O}{\|}}{C}-R_4$$

Col. II $$R_6-\underset{\underset{O}{\|}}{C}-OH$$

Col. III $$R_6-\underset{\underset{O}{\|}}{C}-NH-\underset{\underset{R_2}{|}}{CH}-\underset{\underset{OH}{|}}{CH}-CH_2-\underset{\underset{R_1}{|}}{N}-\underset{\underset{R_3}{|}}{CH}-\underset{\underset{O}{\|}}{C}-\underset{\underset{R_{12}}{|}}{N}-\underset{\underset{R}{|}}{CH}-\underset{\underset{O}{\|}}{C}-R_4$$

| Example | R$_1$ | R$_2$ | R$_3$ | R$_{12}$ |
|---|---|---|---|---|
| 10 | —SO$_2$—⟨phenyl⟩ | —CH$_2$CH(CH$_3$)$_2$ | —CH$_2$CH(CH$_3$)$_2$ | —H |
| 11 | —SO$_2$—⟨phenyl⟩—CH$_3$ | —CH$_2$CH(CH$_3$)$_2$ | —CH$_2$CH(CH$_3$)$_2$ | —H |
| 12 | —(CH$_2$)$_4$NH—CH$_2$—⟨phenyl⟩ | —CH$_2$CH(CH$_3$)$_2$ | —CH(CH$_3$)$_2$ | —H |
| 13 | —CH$_2$—⟨phenyl⟩ | —CH$_3$ | —CH$_3$ | —H |
| 14 | —CH$_2$—⟨phenyl⟩ | —CH$_2$—⟨phenyl⟩ | —CH(CH$_3$)$_2$ | —H |
| 15 | —CH$_2$—⟨phenyl⟩ | —(CH$_2$)$_2$—⟨phenyl⟩ | —CH$_2$CH(CH$_3$)$_2$ | —CH$_3$ |
| 16 | —CH$_2$—⟨phenyl⟩ | —H | —CH$_2$—⟨phenyl⟩ | —CH$_2$—⟨phenyl⟩ |

-continued

| | 25 | | 26 | |
|---|---|---|---|---|
| 17 | —CH₂—C₆H₅ | —CH₂-(indolyl) | —H | —H |
| 18 | —CH₂—C₆H₅ | —CH₂CCl₃ | —(CH₂)₂—C₆H₅ | —H |
| 19 | —CH₂—C₆H₅ | —CH₂—O—CH₂—C₆H₅ | —C₂H₅ | —H |
| 20 | —CH₂—C₆H₅ | —(CH₂)₄—NH—CH₂—C₆H₅ | —CH(CH₃)₂ | —H |
| 21 | —CH₂—C₆H₅ | —CH₂CH(CH₃)₂ | —CH₂CH(CH₃)₂ | —H |
| 22 | —CH₂—C₆H₅ | —CH₂CH(CH₃)₂ | —CH₂—NH—C(=NH)—NH₂—NO₂ | —H |
| 23 | —CH₂—C₆H₅ | —CH₂—S—CH₃ | —CH₂CH(CH₃)₂ | —H |
| 24 | —CH₂—C₆H₅ | —CH₂CH(CH₃)₂ | —CH₂CH(CH₃)₂ | —H |
| 25 | —CH₂—C₆H₅ | —CH₂CH(CH₃)₂ | —CH₂CH(CH₃)₂ | —H |
| 26 | —CH₃ | —CH₂—S—CH₂—C₆H₅ | —CH₃ | —H |
| 27 | —CH₂—C₆H₅ | —CH₂CH(CH₃)₂ | —CH₂CH(CH₃)₂ | —H |

| Example | R | R₄ | R₆ |
|---|---|---|---|
| 10 | —CH(CH₃)₂ | —NH₂ | (H₃C)₃C—O—C(=O)—NH—CH(CH₂—C₆H₅)—C(=O)—NH—CH(CH₂-indolyl)— |

-continued
| | | | |
|---|---|---|---|
| 11 | —CH(CH₃)₂ | —OH | 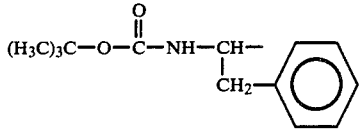 |
| 12 | —CH₂CH(CH₃)₂ | —OCH₃ | 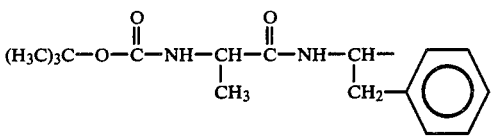 |
| 13 | 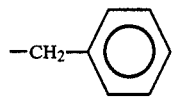 | —OC₂H₅ | 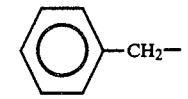 |
| 14 | —CH(CH₃)₂ | 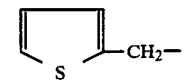 | 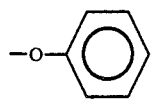 |
| 15 | —H | 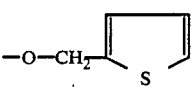 | H₅C₂— |
| 16 | —CH(CH₃)₂ | 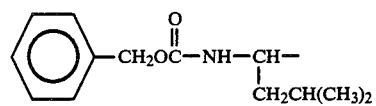 | 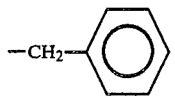 |
| 17 | 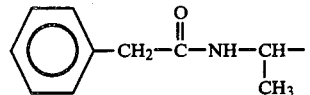 | —OCH₃ | 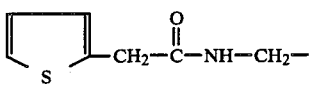 |
| 18 | —CH(CH₃)₂ | —OCH₃ | 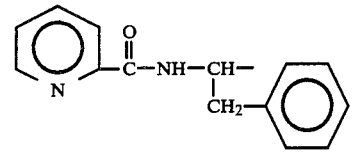 |
| 19 | —CH(CH₃)₂ | —NHCH₃ | 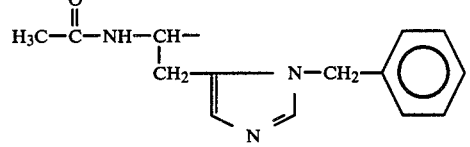 |
| 20 | —CH₃ | —OCH₃ |  |
| 21 | 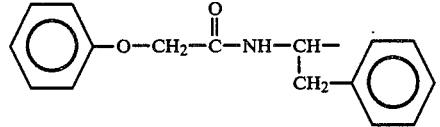 | —OCH₃ | 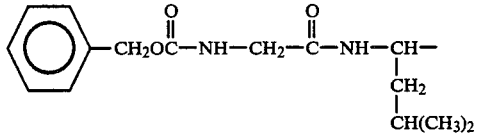 |
| 22 | —CH₂CH(CH₃)₂ | —OCH₃ | |

-continued

| | | | |
|---|---|---|---|
| 23 | 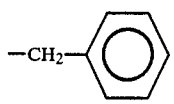 | —OH | 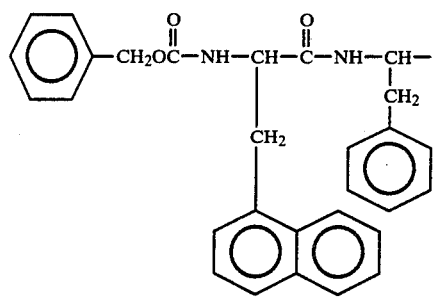 |
| 24 | —CH(CH₃)₂ | | 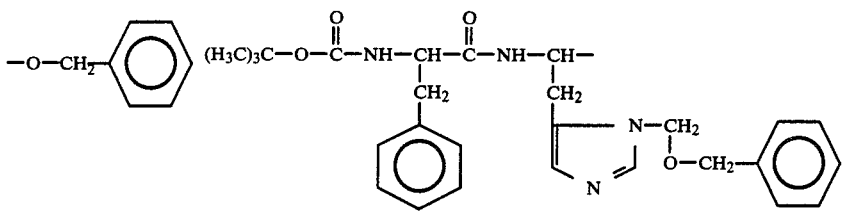 |
| 25 | —CH(CH₃)₂ | —OH | 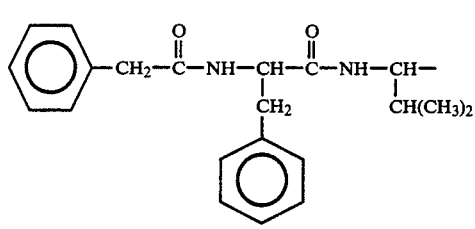 |
| 26 | —CH(CH₃)₂ | —OCH₃ | 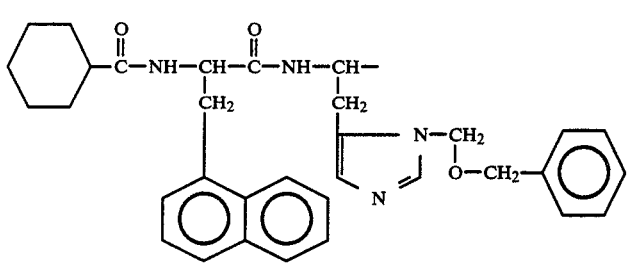 |
| 27 | —CH₂CH(CH₃)₂ | —OCH₃ | 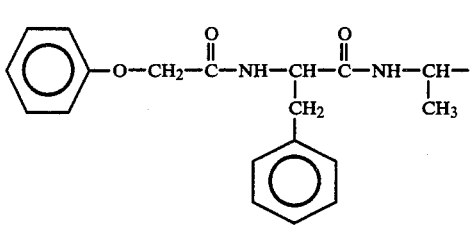 |

The $R_1$ protecting group shown in Examples 12 to 25 and 27, the $R_2$ protecting groups shown in Examples 19, 20, and 26, the $R_3$ protecting group shown in Example 22 are removed as the last step in the synthesis as can the $R_{11}$ group shown in Examples 20, 24 and 26 and the $R_6$ protecting group shown in Examples 16, 22, and 23.

In a similar manner, by employing the corresponding aminoketone of the formula

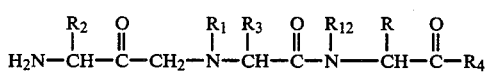

within the procedure of Examples 10 to 27 other compounds within the scope of the invention are obtained.

EXAMPLE 28

1000 tablets each containing the following ingredients:

| | |
|---|---|
| (2R,3S)—N—[N—[3-(L-Histidylamino)-2-hydroxy-5-methylhexyl]-L-leucyl]-L-valine, methyl ester, hydrochloride (1:3.1) | 250 mg. |
| Cornstarch | 100 mg. |
| Gelatin | 20 mg. |
| Avicel (microcrystalline cellulose) | 50 mg. |
| Magnesium stearate | 5 mg. |
| | 425 mg. | are prepared from sufficient bulk quantities by mixing the (2R,3S)-N-[N-[3-(L-histidylamino)-2-hydroxy-5-methylhexyl]-L-leucyl]-L-valine, methyl ester, hydrochloride (1:3.1) and cornstarch with an aqueous solution of the gelatin. The mixture is dried and ground to a fine powder. The Avicel and then the magnesium stearate are admixed with granulation. This mixture is then compressed in a tablet press to form 1000 tablets each containing 250 mg. of active ingredient.

In a similar manner, tablets containing 250 mg. of the product of any of Examples 2 to 27 can be prepared.

A similar procedure can be employed to form tablets containing 500 mg. of active ingredient.

EXAMPLE 29

Two piece #1 gelatin capsules are filled with a mixture of the following ingredients:

| | |
|---|---|
| N—[N—[(3S)—3-[[N—[N—[(1,1-Dimethyl-ethoxy)carbonyl]-L-phenylalanyl]-L-histidyl]amino]-2-hydroxy-5-methylhexyl]-L-leucyl]-L-phenylalanine, methyl ester, acetic acid salt (1:2) | 500 mg. |
| Magnesium stearate | 7 mg. |
| Lactose | 193 mg. |
| | 700 mg. |

In a similar manner capsules containing 500 mg. of the product of any of Examples 1 to 8 and 10 to 27 can be prepared.

EXAMPLE 30

An injectable solution is prepared as follows:

| | |
|---|---|
| (2R,3S)—N—[N—[2-Hydroxy-5-methyl-3-[[N—(L-phenylalanyl)-L-histidyl]amino]butyl]-L-leucyl]-L-valine, methyl ester, trihydrochloride | 1000 g. |
| Methyl paraben | 5 g. |
| Propyl paraben | 1 g. |
| Sodium chloride | 5 g. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 200 mg. of active ingredient per ml. of solution for injection.

In a similar manner, an injectable solution containing 200 mg. of active ingredient per ml. of solution can be prepared for product of any of Examples 1 to 7 and 9 to 27.

EXAMPLE 31

1000 tablets each containing the following ingredients:

| | |
|---|---|
| (2R,3S)—N—[N—[3-[[N—[(1,1-Dimethyl-ethoxy)carbonyl]-L-histidyl]amino]-2-hydroxy-5-methylhexyl]-L-leucyl]-L-valine, methyl ester, acetate salt (1:1) | 500 mg. |
| Avicel | 300 mg. |
| Hydrochlorothiazide | 14.5 mg. |
| Lactose | 113 mg. |
| Cornstarch | 15.5 mg. |

-continued

| | |
|---|---|
| Stearic Acid | 7 mg. |
| | 950 mg. | are prepared from sufficient bulk quantities by slugging the (2R,3S)-N-[N-[3-[[N-[(1,1-dimethylethoxy)carbonyl]-L-histidyl]amino]-2-hydroxy-5-methylhexyl]-L-leucyl]-L-valine, methyl ester, acetate salt (1:1), Avicel, and a portion of the stearic acid. The slugs are ground and passed through a #2 screen, then mixed with the hydrochlorothiazide, lactose, cornstarch, and remainder of the stearic acid. The mixture is compressed into 950 mg. capsule shaped tablets in a tablet press.

In a similar manner, tablets can be prepared containing 500 mg. of the product of any of Examples 1 and 3 to 27.

What is claimed is:

1. A compound of the formula

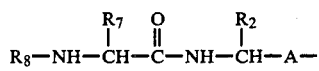

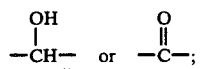

including a pharmaceutically acceptable salt thereof wherein:

$A$ is

$R_4$ is —O—lower alkyl, —O—$(CH_2)_m$—aryl, —OH, —O—$(CH_2)_m$—heterocyclo, or $$\begin{array}{c} H \\ | \\ -N-R_5; \end{array}$$

$R_5$ is hydrogen, lower alkyl, —$(CH_2)_m$—aryl, or —$(CH_2)_m$—heterocyclo;

$R_8$ is hydrogen,

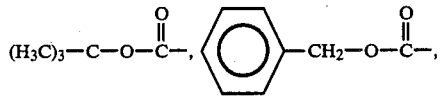

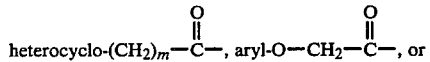

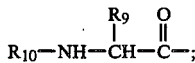

$R_{10}$ is hydrogen,

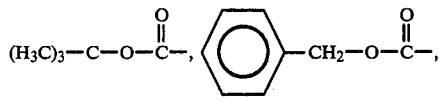

-continued

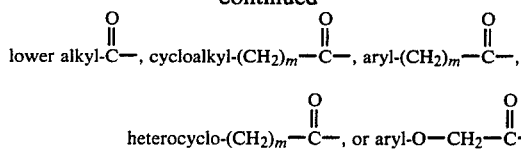

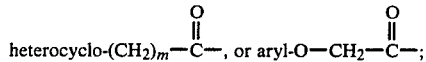

R, $R_2$, $R_3$, $R_7$ and $R_9$ are independently selected from the group consisting of hydrogen, lower alkyl, halo substituted lower alkyl, —$(CH_2)_n$—aryl, —$(CH_2)_n$—heterocyclo, —$(CH_2)_n$—OH, —$(CH_2)_n$—$NH_2$, —$(CH_2)_n$—SH, —$(CH_2)_n$—S—lower alkyl, —$(CH_2)_2$—S—$(CH_2)_2$—$NH_2$,

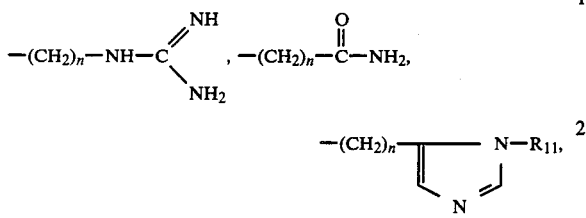

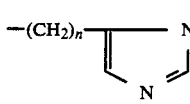

and —$(CH_2)_n$—cycloalkyl;
n is an integer from 1 to 4;
$R_{11}$ is

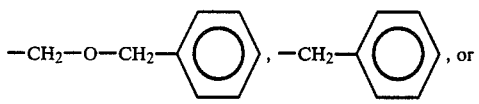

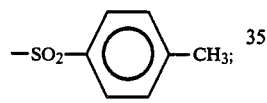

$R_1$ is hydrogen, lower alkyl, —$(CH_2)_n$—aryl, —$(CH_2)_n$—cycloalkyl,

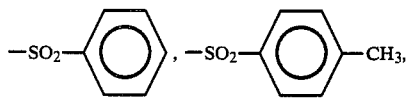

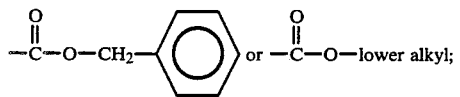

$R_{12}$ is hydrogen, lower alkyl, —$(CH_2)_n$—aryl, or —$(CH_2)_n$—cycloalkyl;
the term lower alkyl refers to straight or branched chain radicals having up to seven carbon atoms;
the term cycloalkyl refers to saturated rings of 4 to 7 carbon atoms;
the term halogen refers to Cl, Br, and F;
the term halo substituted lower alkyl refers to such lower alkyl groups in which one or more hydrogens have been replaced by Cl, Br, or F groups;
the term aryl refers to phenyl, 1-naphthyl, 2-naphthyl, mono substituted phenyl, 1-naphthyl or 2-naphthyl wherein said substituent is lower alkyl of 1 to 4 carbons, lower alkylthio of 1 to 4 carbons, lower alkoxy of 1 to 4 carbons, halogen, hydroxy, amino, —NH—alkyl wherein alkyl is of 1 to 4 carbons, or —N(alkyl)$_2$ wherein alkyl is of 1 to 4 carbons, di or tri substituted phenyl, 1-naphthyl or 2-naphthyl wherein said substituents are methyl, methoxy, methylthio, halogen, or hydroxy; and
the term heterocyclo refers to fully saturated or unsaturated monocyclic rings of 5 or 6 atoms containing one or two O and S atoms and/or one to four N atoms provided that the total number of hetero atoms in the ring is 4 or less and bicyclic rings wherein the five or six membered ring containing O, S and N atoms as defined above is fused to a benzene ring.

2. A compound of claim 1 wherein:
A is

3. A compound of claim 1 wherein:
A is

4. A compound of claim 3 wherein:
$R_1$ is hydrogen,

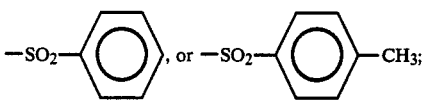

$R_2$ is straight or branched chain lower alkyl of 1 to 4 carbons, benzyl, phenethyl, or

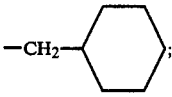

$R_3$ is hydrogen, straight or branched chain lower alkyl of 1 to 4 carbons, benzyl or phenethyl;
$R_{12}$ is hydrogen;
R is straight or branched chain lower alkyl of 1 to 4 carbons, benzyl, or phenethyl;
$R_4$ is —O—lower alkyl wherein lower alkyl is straight or branched chain of 1 to 4 carbons;
$R_7$ is

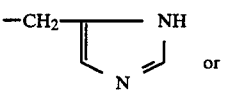

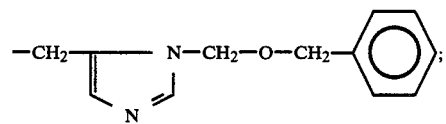

$R_8$ is hydrogen,

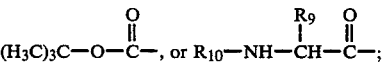

R₉ is —(CH₂)ₙ—aryl wherein aryl is phenyl or 1-naphthyl and n is one or two; and R₁₀ is hydrogen,

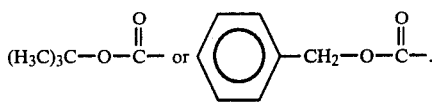

5. A compound of claim 4 wherein
R₁ is hydrogen;
R₂ is —CH₂—CH(CH₃)₂;
R₃ is —CH₂—CH(CH₃)₂ or —CH(CH₃)₂;
R is —CH(CH₃)₂ or benzyl;
R₄ is —OCH₃;
R₉ is

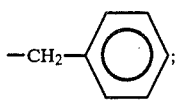

and
R₁₀ is hydrogen or

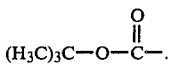

6. A compound of claim 5 wherein:
R is —CH(CH₃)₂;
R₃ is —CH₂—CH(CH₃)₂;
R₇ is

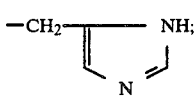

and
R₈ is hydrogen.

7. The compound of claim 6, (2R,3S)-N-[N-[3-(L-histidylamino)-2-hydroxy-5-methylhexyl]-L-leucyl]-L-valine, methyl ester, hydrochloride (1:3.1).

8. The compound of claim 6, (2S,3S)-N-[N-[3-(L-histidylamino)-2-hydroxy-5-methylhexyl]-L-leucyl]-L-valine, methyl ester, hydrochloride (1:3).

9. A compound of claim 5 wherein:
R is —CH(CH₃)₂;
R₃ is —CH₂—CH(CH₃)₂;
R₇ is

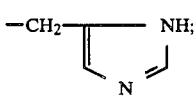

and
R₈ is

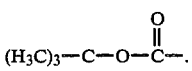

10. The compound of claim 9, (2R,3S)-N-[N-[3-[[N-[(1,1-dimethylethoxy)carbonyl]-L-histidyl]-amino]-2-hydroxy-5-methylhexyl]-L-leucyl]-L-valine, methyl ester, acetate salt (1:1).

11. The compound of claim 9, (2S,3S)-N-[N-[3-[[N-[(1,1-dimethylethoxy)carbonyl]-L-histidyl]amino]-2-hydroxy-5-methylhexyl]-L-leucyl]-L-valine, methyl ester.

12. A compound of claim 5 wherein:
R is —CH(CH₃)₂;
R₃ is —CH₂—CH(CH₃)₂;
R₇ is

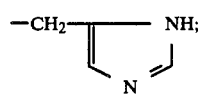

R₈ is

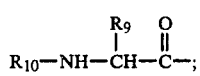

R₉ is

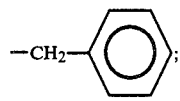

and
R₁₀ is

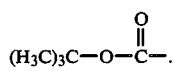

13. The compound of claim 12, (2S,3S)-N-[N-[3-[[N-[N-[(1,1-dimethylethoxy)carbonyl]-L-phenylalanyl]-L-histidyl]amino]-2-hydroxy-5-methylhexyl]-L-leucyl]-L-valine, methyl ester, monoacetate salt.

14. The compound of claim 12, (2R,3S)-N-[N-[3-[[N-[N-[(1,1-dimethylethoxy)carbonyl]-L-phenylalanyl]-L-histidyl]amino]-2-hydroxy-5-methylhexyl]-L-leucyl]-L-valine, methyl ester, monoacetate salt.

15. A compound of claim 5 wherein:
R is —CH(CH₃)₂;
R₃ is —CH₂—CH(CH₃)₂;
R₇ is

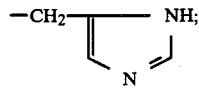

R₈ is

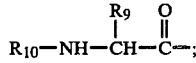

R₉ is

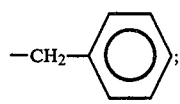

and
R₁₀ is hydrogen.

16. The compound of claim 15, (2S,3S)-N-[N-[2-hydroxy-5-methyl-3-[[N-(L-phenylalanyl)-L-histidyl]amino]butyl]-L-leucyl]-L-valine, methyl ester, trihydrochloride.

17. The compound of claim 15, (2R,3S)-N-[N-[2-hydroxy-5-methyl-3-[[N-(L-phenylalanyl)-L-histidyl]amino]butyl]-L-leucyl]-L-valine, methyl ester trihydrochloride.

18. A compound of claim 6 wherein:
R is benzyl;
R$_3$ is —CH$_2$—CH(CH$_3$)$_2$;
R$_7$ is

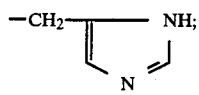

R$_8$ is

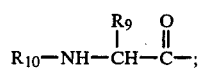

R$_9$ is

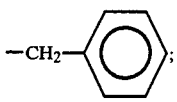

and
R$_{10}$ is

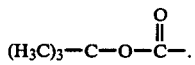

19. The compound of claim 18, N-[N-[(3S)-3-[[N-[N-[(1,1-dimethylethoxy)carbonyl]-L-phenylalanyl]-L-histidyl]amino]-2-hydroxy-5-methylhexyl]-L-leucyl]-L-phenylalanine, methyl ester, acetic acid salt (1:2).

20. A composition for treating hypertension in a mammalian specie comprising a pharmaceutically acceptable carrier and an anti-hypertensively effective amount of a compound of claim 1.

21. A method of treating hypertension in a mammalian specie which comprises administering an anti-hypertensively effective amount of the composition of claim 20.

* * * * *